(12) United States Patent
Li et al.

(10) Patent No.: US 8,580,247 B2
(45) Date of Patent: Nov. 12, 2013

(54) PS-1 ANTIBODIES IN COMBINATION WITH A CYTOKINE-SECRETING CELL AND METHODS OF USE THEREOF

(75) Inventors: Betty Li, San Francisco, CA (US); Karin Jooss, Bellevue, WA (US); Alan J. Korman, Piedmont, CA (US)

(73) Assignees: Aduro GVAX Inc., Berkeley, CA (US); Medarex, Inc., Milpitas, CA (US)

( * ) Notice: Subject to any disclaimer, the term of this patent is extended or adjusted under 35 U.S.C. 154(b) by 0 days.

(21) Appl. No.: 13/619,699

(22) Filed: Sep. 14, 2012

(65) Prior Publication Data

US 2013/0022600 A1 Jan. 24, 2013

Related U.S. Application Data

(60) Division of application No. 12/839,163, filed on Jul. 19, 2010, now Pat. No. 8,287,856, which is a continuation of application No. 12/178,122, filed on Jul. 23, 2008, now abandoned.

(60) Provisional application No. 60/961,743, filed on Jul. 23, 2007.

(51) Int. Cl.
*A61K 39/00* (2006.01)

(52) U.S. Cl.
USPC ..................................... 424/93.2; 424/135.1

(58) Field of Classification Search
None
See application file for complete search history.

(56) References Cited

U.S. PATENT DOCUMENTS

| | | | |
|---|---|---|---|
| 4,474,893 A | 10/1984 | Reading | |
| 4,714,681 A | 12/1987 | Reading | |
| 4,925,648 A | 5/1990 | Hansen et al. | |
| 5,078,996 A | 1/1992 | Colon, III et al. | |
| 5,098,702 A | 3/1992 | Zimmerman et al. | |
| 5,225,348 A | 7/1993 | Nagata et al. | |
| 5,266,491 A | 11/1993 | Nagata et al. | |
| 5,436,146 A | 7/1995 | Shenk et al. | |
| 5,573,920 A | 11/1996 | Randle | |
| 5,601,819 A | 2/1997 | Wong et al. | |
| 5,637,483 A | 6/1997 | Dranoff et al. | |
| 5,665,577 A | 9/1997 | Sodroski et al. | |
| 5,753,500 A | 5/1998 | Shenk et al. | |
| 5,904,920 A | 5/1999 | Dranoff et al. | |
| 5,955,331 A | 9/1999 | Danos et al. | |
| 5,981,276 A | 11/1999 | Sodroski et al. | |
| 5,985,290 A | 11/1999 | Jaffee et al. | |
| 6,033,674 A | 3/2000 | Jaffee et al. | |
| 6,037,177 A | 3/2000 | Snyder | |
| 6,040,183 A | 3/2000 | Ferrari et al. | |
| 6,093,570 A | 7/2000 | Ferrari et al. | |
| 6,350,445 B1 | 2/2002 | Jaffee et al. | |
| 6,428,953 B1 | 8/2002 | Naldini et al. | |
| 6,464,973 B1 | 10/2002 | Levitsky et al. | |
| 6,506,604 B2 | 1/2003 | Finer et al. | |
| 2005/0002916 A1 | 1/2005 | Jooss et al. | |
| 2009/0217401 A1* | 8/2009 | Korman et al. | .................. 800/18 |

FOREIGN PATENT DOCUMENTS

| | | |
|---|---|---|
| WO | 91/00360 | 1/1991 |
| WO | 92/05793 | 4/1992 |
| WO | 92/08802 | 5/1992 |
| WO | 93/17715 | 9/1993 |
| WO | 97/34631 | 9/1997 |
| WO | 98/46728 | 10/1998 |
| WO | 00/72686 | 12/2000 |
| WO | 2006/121168 | 11/2006 |

OTHER PUBLICATIONS

Dranoff et al (PNAS, 1993, 90:3539-3543, IDS).*
Agata et al. 1996 "Expression of the PD-1 Antigen on the Surface of Stimulated Mouse T and B Lymphocytes" International Immunology vol. 8(5):765-772.
Altschul et al. 1990 "Basic Local Alignment Search Tool" J. Mol. Biol. vol. 215:403-410.
Altschul et al. 1997 "Gapped BLAST and PSI-BLAST: A New Generation of Protein Database Search Programs" Nucleic Acids Research vol. 25(17):3389-3402.
Aoki et al. 1992 "Expression of Murine Interleukin 7 in a Murine Glioma Cell Line Results in Reduced Tumorigenicity In Vivo" Proc. Natl. Acad. Sci. vol. 89: 3850-3854.
Armstrong et al. 2002 "Cytokine Modified Tumor Vaccines" Surgical Oncology Clinics of North America vol. 11 (3):681-696.
Ahser et al. 1991 "Murine Tumor Cells Transduced with the Gene for Tumor Necrosis Factor" J. Immunol. vol. 146:3227-3234.
Beal et al. 1991 "Second Structural Motif for Recognition of DNA by Oligonucleotide-Directed Triple Helix Formation" Science vol. 251:1360:1363.
Berkelhammer et al. 1982 "Development of a New Melanoma Model in C57BL/6 Mice" Cancer Research vol. 42:3157-3163.
Betts et al. 2003 "Sensitive and Viable Identification of Antigen-Specific CD8+ T Cells by a Flow Cytometric Assay for Degranulation" Journal of Immunological Methods vol. 281(1-2):65-78.
Bird et al. 1988 "Single-Chain Antigen-Binding Proteins" Science vol. 242:423-426.

(Continued)

*Primary Examiner* — Laura B Goddard
(74) *Attorney, Agent, or Firm* — Michael A. Whittaker; Acuity Law Group, P.C.

(57) ABSTRACT

The present invention relates to a method of enhancing the anti-tumor response in a mammal. More particularly, the invention is concerned with combinations comprising a cytokine-secreting cell and an anti-PD-1 antibody, and methods of administering the combination for enhanced immune response to tumor cells in a patient with a cancer.

19 Claims, 14 Drawing Sheets

(56) References Cited

OTHER PUBLICATIONS

Blank et al. 2005 "Interaction of PD-L1 on Tumor Cells with PD-1 on Tumor-Specific T Cells as a Mechanism of Immune Evasion: Implications for Tumor Immunotherapy" Cancer Immunol. Immunother. vol. 54(4):307-314.
Bodey et al. 2000 "Failure of Cancer Vaccines: The Significant Limitations of this Approach to Immunotherapy" Anticancer Research vol. 20(4):2665-2676.
Brown et al. 2003 "Blockade of Programmed Death-1 Ligands on Dendritic Cells Enhances T Cell Activation and Cytokine Production" The Journal of Immunology vol. 170:1257-1266.
Cantrell et al. 1985 "Cloning Sequence and Expression of a Human Granulocyte/Macrophage Colony-Stimulating Factor" PNAS vol. 82:6250-6254.
Chang et al. 2000 "Immunogenetic Therapy of Human Melanoma Utilizing Autologous Tumor Cells Transduced to Secrete Granulocyte-Macrophage Colony-Stimulating Factor" Human Gene Therapy vol. 11:839-850.
Cooney et al. 1988 "Site-Specific Oligonucleotide Binding Represses Transcription of the Human c-myc Gene In Vitro" Science vol. 241:456-459.
Darrow et al. 1989 "The Role of HLA Class I Antigens in Recognition of Melanoma Cells by Tumor-Specific Cytotoxic T Lymphocytes" The Journal of Immunology vol. 142:3329-3335.
Dong et al. 2002 "Tumor-Associated B7-H1 Promotes T-Cell Apoptosis: A Potential Mechanism of Immune Evasion" Nature Medicine vol. 8:793-800.
Dranoff et al. 1993 "Vaccination with Irradiated Tumor Cells Engineered to Secrete Murine Granulocyte-Macrophage Colony-Stimulating Factor Stimulates Potent Specific and Long-Lasting Anti-Tumor Immunity" PNAS vol. 90:3539-3543.
Dummer et al. 2001 "GVAX Cell Genesys" Current Opin. Investig. Drugs vol. 2(6):844-848.
Dunn et al. 2002 "Cancer Immunoediting: From Immuno-Survellance to Tumor Escape" Nat. Immunol. vol. 3 (11):991-998.
Fearon et al. 1990 "Interleukin-2 Production by Tumor Cells Bypasses T Helper Function in the Generation of an Antitumor Response" Cell vol. 60:397-403.
Freeman et al. 2000 "Engagement of the PD-1 Immunoinhibitory Receptor by a Novel B7 Family Members Leads to Negative Regulation of Lymphocyte Activation" J. Exp. Med. vol. 192:1027-1034.
Gansbacher et al. 1990 "Retroviral Vector-Mediated γ-Inteferon Gene Transfer Into Tumor Cells Generates Potent and Long Lasting Antitumor Immunity" Cancer Research vol. 50:7820-7825.
Gansbacher et al. 1990 "Interleukin 2 Gene Transfer into Tumor Cells Abrogates Tumorigenicity and Induces Protective Immunity" J. Exp. Med. vol. 172:1217-1224.
Goldberg et al. 2007 "Role of PD-1 and its Ligand B7-H1 in Early Fate Decisions of CD8 T Cells" Blood vol. 110 (1):186-192.
Golumbeck et al. 1991 "Treatment of Established Renal Cancer by Tumor Cells Engineered to Secrete Interleukin-4" Science vol. 254:713-716.
Griswold D.P. 1972 "Consideration of the Subcutaneously Implanted B16 Melanoma as a Screening Model for Potential Anticancer Agents" Cancer Chemotherapy Reports Part 2 vol. 3(1):315-324.
Guo et al. 1996 "Evaluation of Promoter Strength for Hepatic Gene Expression In Vivo Following Adenovirus-Mediated Gene Transfer" Gene Therapy vol. 3(9):802-810.
Havell et al. 1988 "The Antitumor Function of Tumor Necrosis Factor (TNF)" J. Exp. Med. vol. 167:1067-1085.
Hock et al. 1991 "Interleukin 7 Induces CD4+ T Cell-Dependent Tumor Rejection" J. Exp. Med. vol. 174:1291-1298.
Hom et al. 1991 "Common Expression of Melanoma Tumor-Associated Antigens Recognized by Human Tumor Infiltrating Lymphocytes: Analysis by Human Lymphocyte Antigen Restriction" Journal of Immunotherapy vol. 10:153-164.
Hu et al. 2002 "Development of Antitumor Immune Responses in Reconstituted Lymphopenic Hosts" Cancer Research vol. 62:3914-3919.
Huang et al. 1994 "Role of Bone Marrow-Derived Cells in Presenting MHC Class I-Restricted Tumor Antigens" Science vol. 264:961-965.
Huebner et al. 1985 "The Human Gene Encoding GM-CSF is a 5q21-q32 the Chromosome Region Deleted in the 5q-Anomaly" Science vol. 230(4731):1282-1285.
Huston et al. 1988 "Protein Engineering of Antibody binding Sites: Recovery of Specific Activity in an Anti-Digoxin Single-Chain Fv Analogue Produced in *Escherichia coli*" PNAS vol. 85:5879-5883.
Ill et al. 1997 "Optimization of the Human Factor VIII Complementary DNA Expression Plasmid for Gene Therapy of Hemophilia A" Blood Coagul Fibrinolysis vol. 8 Supp. vol. 2:S23-30.
Ishida et al. 1992 "Induced Expression of PD-1 a Novel Member of the Immunoglobulin Gene Superfamily Upon Programmed Cell Death" The EMBO Journal vol. 11(11):3887-3895.
Iwai et al. 2002 "Microanatomical Localization of PD-1 in Human Tonsils" Immunology Letters vol. 83:215-220.
Jaffee et al. 2001 "Novel Allogeneic Granulocyte-Macrophage Colony-Stimulating Factor-Secreting Tumor Vaccine for Pancreatic Cancer: A Phase I Trial of Safety and Immune Activation" Journal of Clinical Oncology vol. 19 (1):145-156.
Jaffee et al. 1995 "Gene Therapy: Its Potential Applications in the Treatment of Renal-Cell Carcinoma" Seminars in Oncology vol. 22:81-91.
Kawakami et al. 1992 "Shared Human Melanoma Antigens Recognition by Tumor-Infiltrating Lymphocytes in HLA-A2.1-Transfected Melanomas" J. Immunol. vol. 148:638-643.
Kim et al. 1990 "Use of the Human Elongation Factor 1α Promoter as a Versatile and Efficient Expression System" Gene vol. 91(2):217-223.
Klein et al. 1976 "Properties of the K562 Cell Line Derived From a Patient with Chronic Myeloid Leukemia" Intl. J. Cancer vol. 18:421-431.
Kostelny et al. 1992 "Formation of a Bispecific Antibody by the Use of Leucine Zippers" M. Immunol. vol. 148:1547-1553.
Lee et al. 1979 "Complexes Formed by (pyrimidine)n (purine)n DNAs on Lowering the pH are Three-Stranded" Nucleic Acids Research vol. 6:3073-3091.
Lee et al 1997 "Genetic Immunotherapy of Established Tumors with Adenovirus-Murine Granulocyte-Macrophage Colony-Stimulating Factor" Human Gene Therapy vol. 8:187-193.
Lozzio et al. 1975 "Human Chronic Myelogenous Leukemia Cell-Line with Positive Philadelphia Chromosome" Blood vol. 45(3):321-334.
Nagai et al., 1998, "Irradiated Tumor Cells Adenovirally Engineered to Secrete Granulocyte/Macrophage-Colony-Stimulating Factor Established Antitumor Immunity and Eliminate Pre-Existing Tumors in Syngeneic Mice," Cancer Immunol. Immunoth., vol. 47:72-80.
Nishimura et al., 1999, "Development of Lupus-Like Autoimmune Diseases by Disruption of the PD-1 Gene Encoding an ITIM Motif-Carrying Immunoreceptor," Immunity, vol. 11:141-151.
Nishimura et al., 2001, "Autoimmune Dilated Cardiomyopathy in PD-1 Receptor-Deficient Mice," Science, vol. 291:319-322.
Okano et al., 1991, "Myelin Basic Protein Gene and the Function of Antisense RNA in its Repression in Myelin-Deficient Mutant Mouse," Journal of Neurochemistry, vol. 56:560-567.
Okazaki et al., 2002, "New Regulatory Co-Receptors: Inducible Co-Stimulator and PD-1," Curr. Opin. Immunol., vol. 14:779-782.
Plaskin et al., 1994, "Effective Anti-Metastatic Melanoma Vaccination with Tumor Cells Transfected with MHC Genes and/or Infected with Newcastle Disease Virus (NDV)," Int. J. Cancer, vol. 59:796-801.
Porgador et al., 1994, "Immunotherapy of Tumor Metastasis via Gene Therapy," Nat. Immun., vol. 13 (2-3):113-130.
Quezada et al., 2006, "CTLA4 Blockade and GM-CSF Combination Immunotherapy Alters the Intratumor Balance of Effector and Regulatory T Cells," J. Clin. Invest., vol. 116(7):1935-1945.
Rivera et al., 1996, "A Humanized System for Pharmacologic Control of Gene Expression," Nature Med., vol. 2 (9)1028-1032.
Rubio et al., 2003, "Ex Vivo Identification, Isolation and Analysis of Tumor-Cytolytic T Cells," Nature Medicine, vol. 9 (11):1377-1382.
Salgia et al., 2003, "Vaccination with Irradiated Autologous Tumor Cells Engineered to Secrete Granulocyte-Macrophage Colony-Stimulating Factor Augments Antitumor Immunity in Some Patients

(56) References Cited

OTHER PUBLICATIONS with Metastatic Non-Small-Cell Lung Carcinoma," Journal of Clinical Oncology, vol. 21(4):624-630.
Salvadori et al., 1995, "B7-1 Amplifies the Response to Interleukin-2-Secreting Tumor Vaccines In Vivo, but Fails to Induce a Response by Naïve Cells In Vitro," Human Gene Therapy, vol. 6:1299-1306.
Samulski et al., 1989, "Helper-Free Stocks of Recombinant Adeno-Associated Viruses: Normal Integration Does Not Require Viral Gene Expression," Virol., vol. 63:3822-3828.
Sawyer et al., 2002, "Src Homology-2 Inhibitors: Peptidomimetic and Nonpeptide," Min. Rev. Med. Chem., vol. 2 (5):475-488.
Schroder et al., 2004, "Interferon-γ: An Overview of Signals, Mechanisms and Functions," Journal of Leukocyte Biology, vol. 75(2):163-189.
Shinohara et al., 1994, "Structure and Chromosomal Localization of the Human PD-1 Gene (PDCD1)," Genomics, vol. 23:704-706.
Simons et al., 1997, "Bioactivity of Autologous Irradiated Renal Cell Carcinoma Vaccines Generated by ex Vivo Granulocyte-Macrophage Colony-Stimulating Factor Gene Transfer," Cancer Research, vol. 57:1537-1546.
Smyth et al., 2001 "A Fresh Look at Tumor Immunosurveillance and Immunotherapy," Nat. Immunol., vol. 2 (4):293-299.
Strome et al., 2003, "B7-H1 Blockade Augments Adoptive T-Cell Immunotherapy for Squamous Cell Carcinoma," Cancer Research, vol. 63:6501-6505.
Teng et al., 1991, "Long-Term Inhibition of Tumor Growth by Tumor Necrosis Factor in the Absence of Cachexia or T-Cell Immunity," PNAS, vol. 88:3535-3539.
Thompson et al., 2007, "PD-1 is Expressed by Tumor-Infiltrating Immune Cells and is Associated with Poor Outcome for Patients with Renal Cell Carcinoma," Clin. Cancer Res., vol. 13(6):1757-5761.
Tutt et al., 1991, "Trispecific F(ab')3 Derivatives that Use Cooperative Signaling via the TCR/CD3 Complex and CD2 to Activate and Redirect Resting Cytotoxic T Cells," J. Immunol., vol. 147:60-69.
Ward et al., 1989, "Binding Activities of a Repertoire of Single Immunoglobulin Variable Domains Secreted from *Escherichia coli*," Nature, vol. 341:544-546.
Wintterele et al., 2003, "Expression of the B7-Related Molecule B7-H1 by Glioma Cells: A Potential Mechanism of Immune Paralysis," Cancer Research, vol. 63:7462-7467.
Ye et al., 1999, "Regulated Delivery of Therapeutic Proteins After in Vivo Somatic Cell Gene Transfer," Science, vol. 283:88-91.
PCT International Search Report dated Dec. 22, 2008, for International Application No. PCT/US2008/08925, filed Jul. 23, 2008.
Borello et al. (Cytokine & Growth Factor Reviews, 2002, 13:185-193).

\* cited by examiner

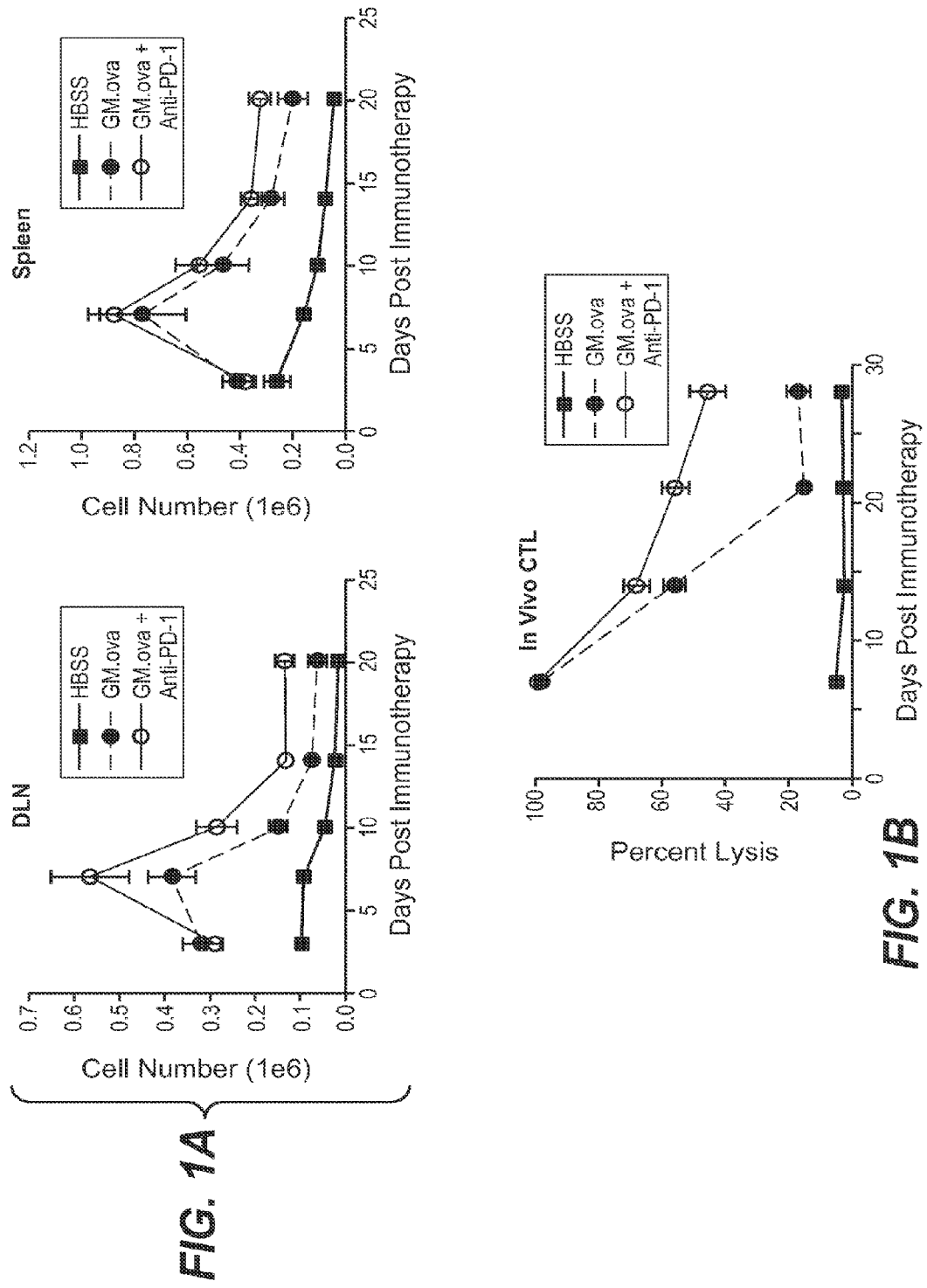

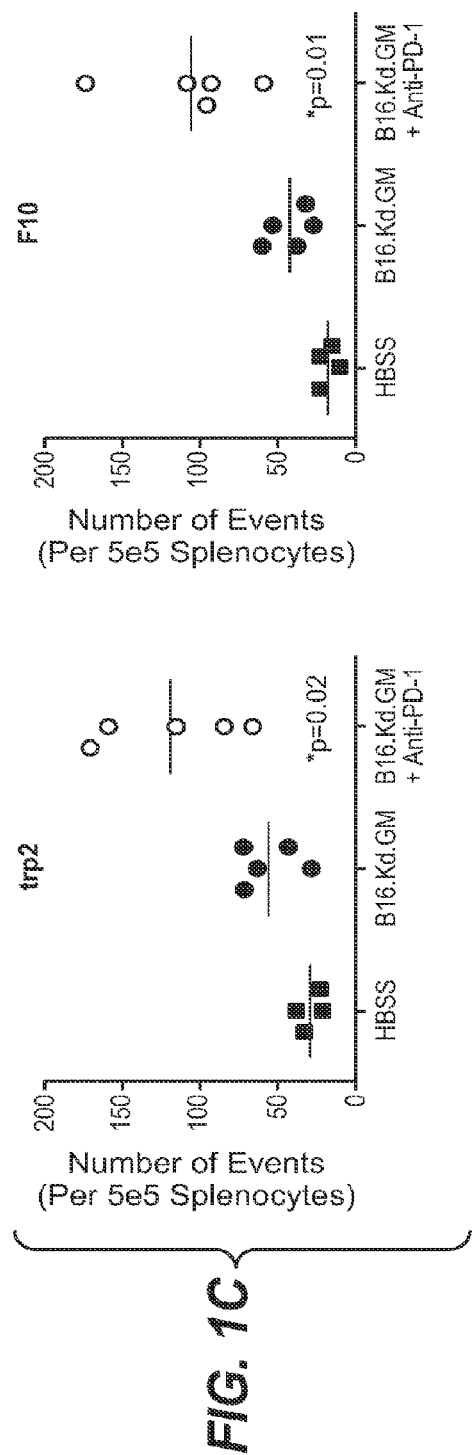
FIG. 1C
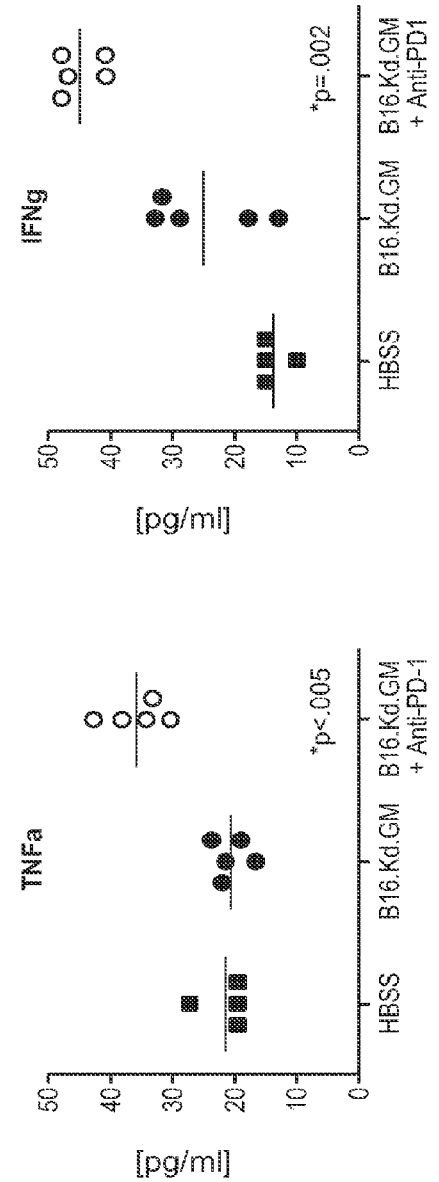
FIG. 2A
FIG. 2B

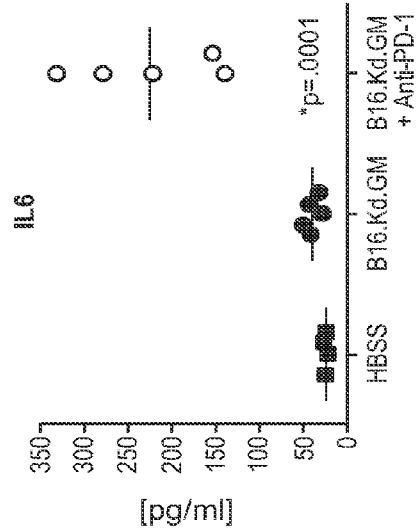
FIG. 2C
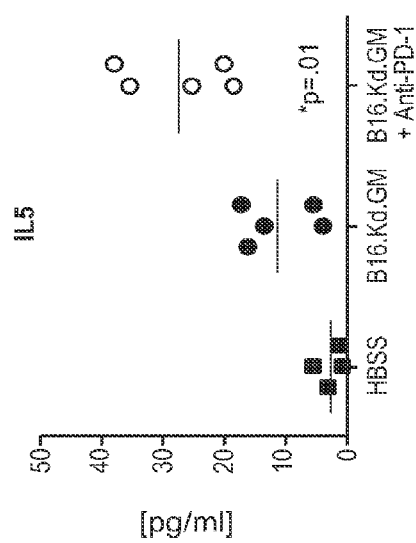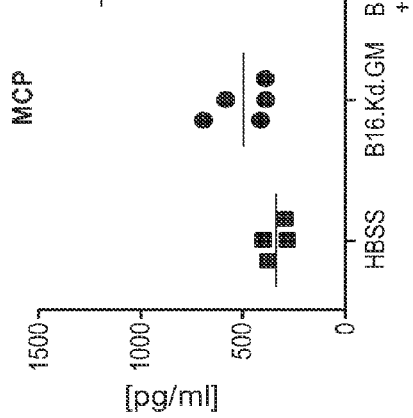
FIG. 2D
FIG. 2E
FIG. 2F

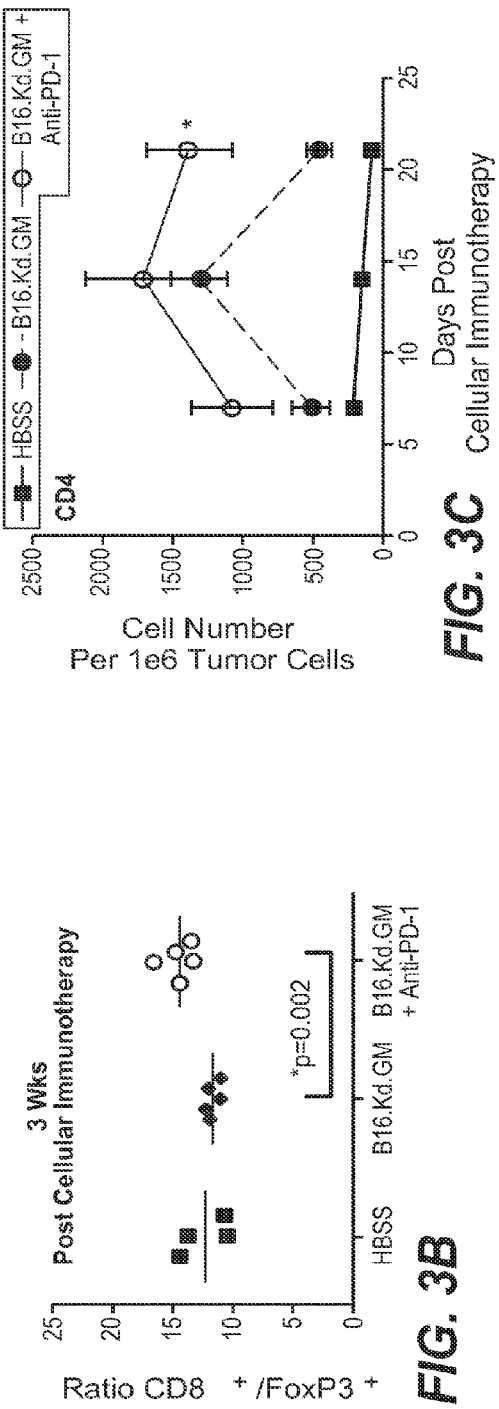

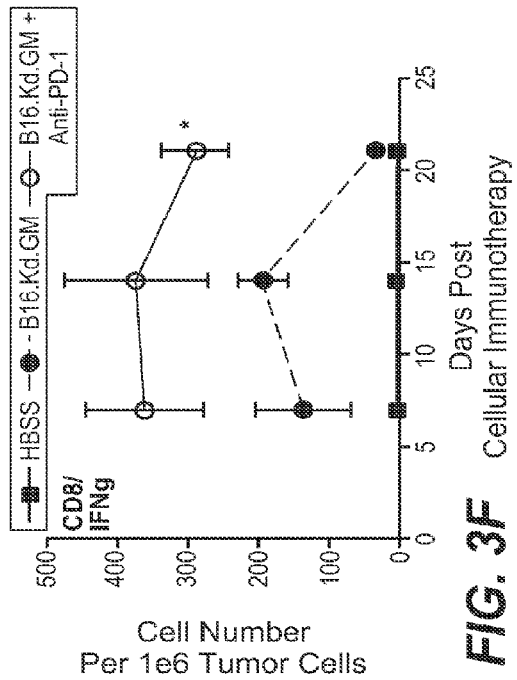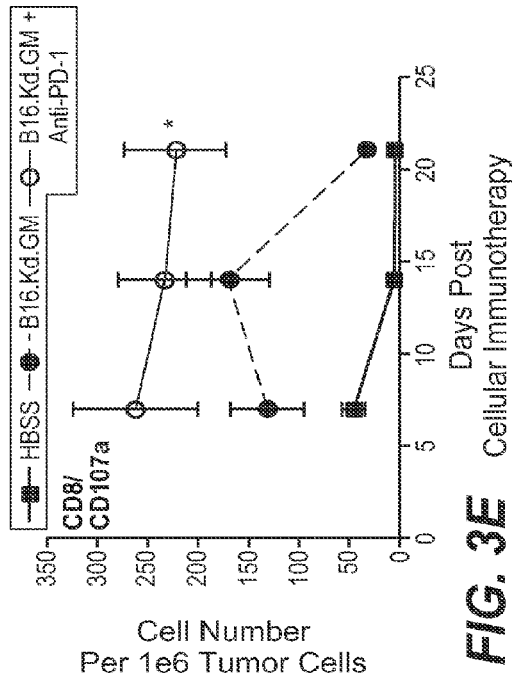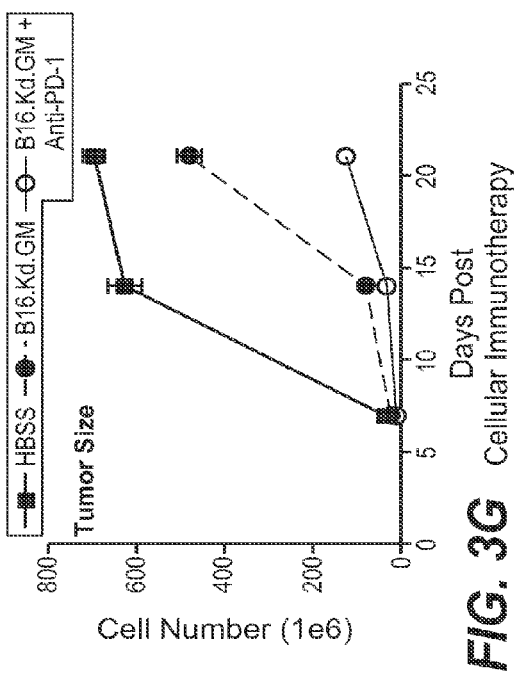

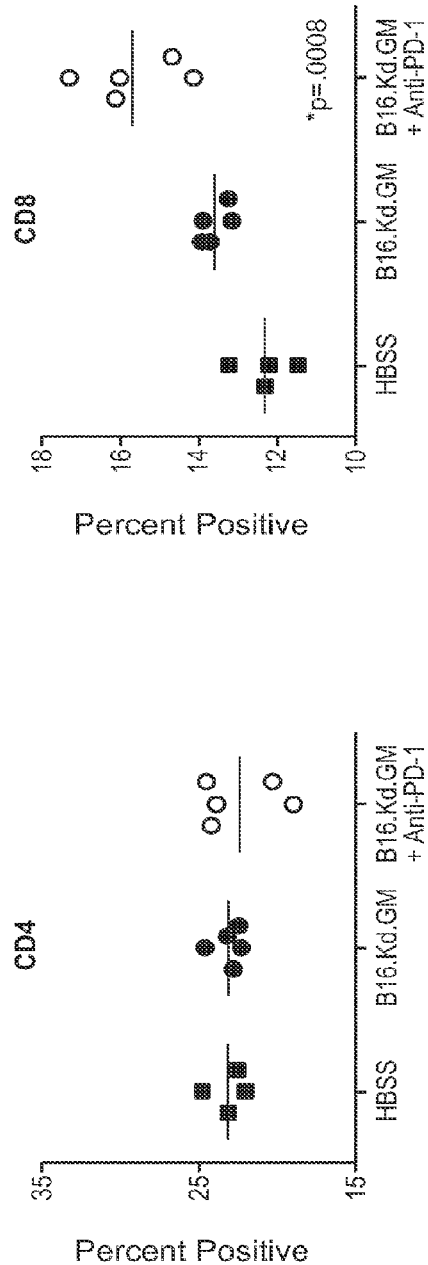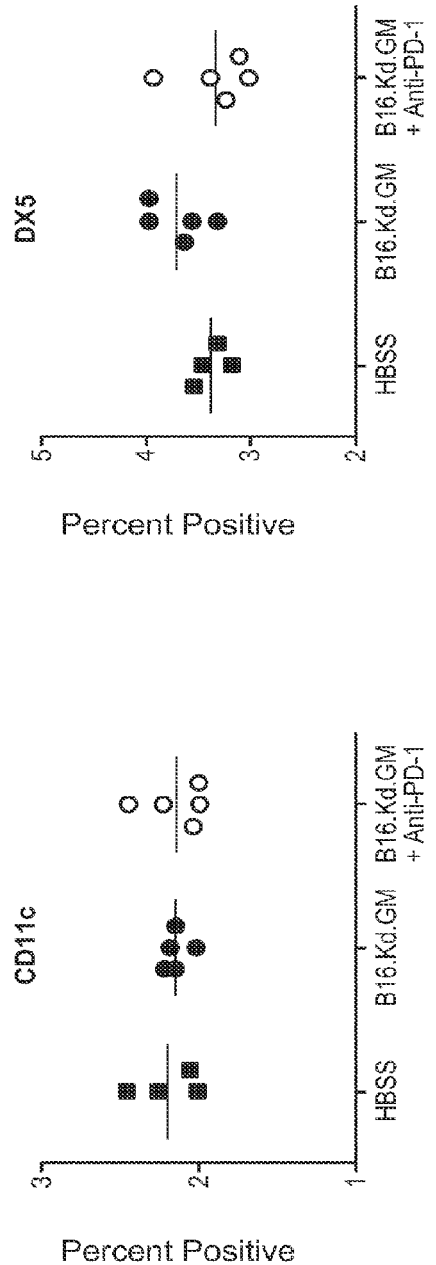
FIG. 6A  FIG. 6B  FIG. 6C  FIG. 6D

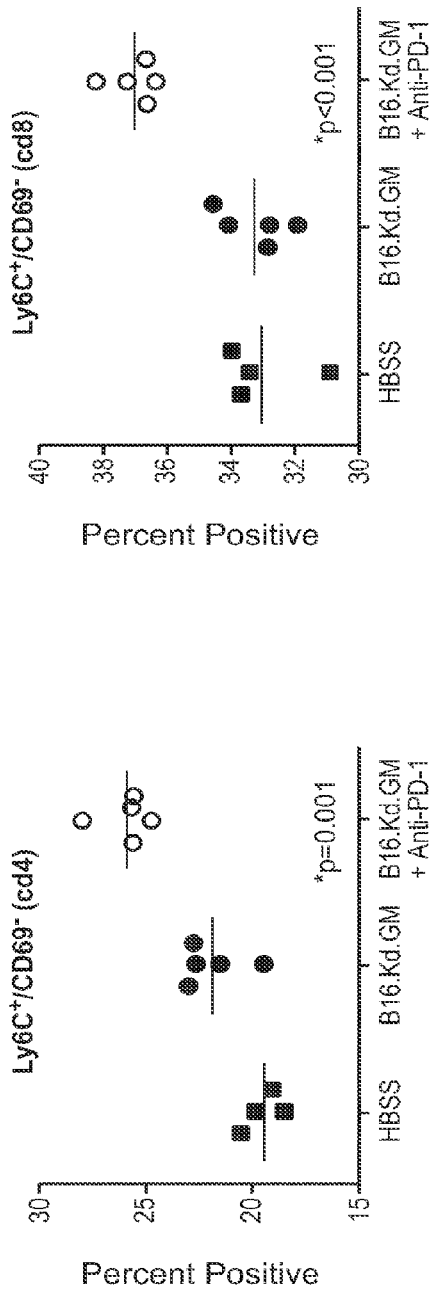
FIG. 7A
FIG. 7B
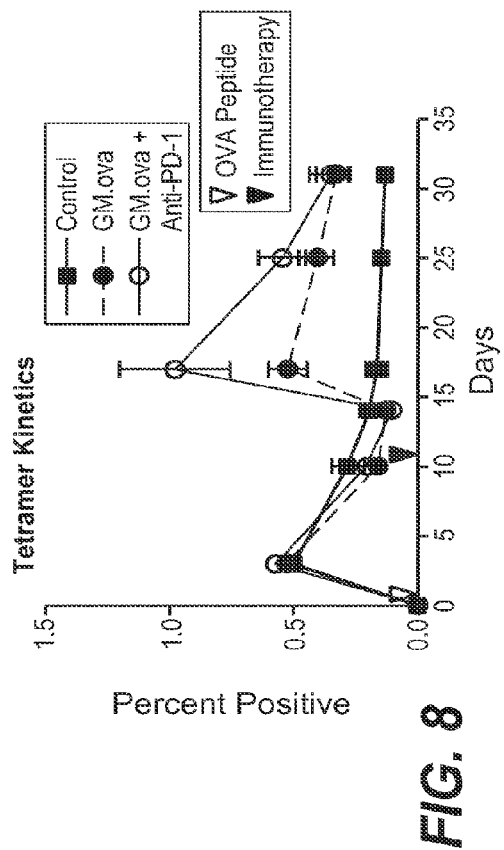
FIG. 8

US 8,580,247 B2

PS-1 ANTIBODIES IN COMBINATION WITH A CYTOKINE-SECRETING CELL AND METHODS OF USE THEREOF

This application is a divisional of U.S. application Ser. No. 12/839,163, filed Jul. 19, 2010, which is a continuation of U.S. application Ser. No. 12/178,122, filed Jul. 23, 2008, now abandoned, which claims benefit of priority of U.S. provisional application No. 60/961,743, filed on Jul. 23, 2007, the contents of which are hereby incorporated by reference in their entireties.

FIELD OF THE INVENTION

The present invention relates to methods and compositions for enhancing anti-tumor protection in a mammal. More particularly, the invention is concerned with combinations comprising an antibody that specifically binds to human Programmed Death 1 (PD-1) and a cytokine-secreting cell, and methods of administering the combination for enhanced generation of an immune response to tumor cells in a patient.

BACKGROUND OF THE INVENTION

The immune system plays a critical role in the pathogenesis of a wide variety of cancers. When cancers progress, it is widely believed that the immune system either fails to respond sufficiently or fails to respond appropriately, allowing cancer cells to grow. Currently, standard medical treatments for cancer, including chemotherapy, surgery, radiation therapy and cellular therapy, have clear limitations with regard to both efficacy and toxicity. To date, these approaches have met with varying degrees of success dependent upon the type of cancer, general health of the patient, stage of disease at the time of diagnosis, etc. Improved strategies that combine specific manipulation of the immune response to cancer in combination with standard medical treatments may provide a means for enhanced efficacy and decreased toxicity.

The use of autologous cancer cells as immunotherapies to augment anti-tumor immunity has been explored for some time (Oettgen et al., "The History of Cancer Immunotherapy", In: Biologic Therapy of Cancer, Devita et al. (eds.) J. Lippincot Co., pp 87-199, 1991). However, due to the weak immunogenicity of many cancers, down regulation of MHC molecules, the lack of adequate costimulatory molecule expression and secretion of immunoinhibitory cytokines by cancer cells, the response to such immunotherapies has not resulted in long term efficacy. See, e.g., Armstrong T D and Jaffee E M, Surg Oncol Clin N Am. 11(3):681-96, 2002 and Bodey B et al, Anticancer Res 20(4):2665-76, 2000.

Numerous cytokines have been shown to play a role in regulation of the immune response to tumors. For example, U.S. Pat. No. 5,098,702 describes using combinations of TNF, IL-2 and IFN-beta in synergistically effective amounts to combat existing tumors. U.S. Pat. Nos. 5,078,996, 5,637,483 and 5,904,920 describe the use of GM-CSF for treatment of tumors. However, direct administration of cytokines for cancer therapy may not be practical, as they are often systemically toxic. (See, for example, Asher et al., J. Immunol. 146: 3227-3234, 1991 and Havell et al, J. Exp. Med. 167: 1067-1085, 1988.)

An expansion of this approach involves the use of genetically modified tumor cells which express cytokines locally at the immunotherapy site. Activity has been demonstrated in tumor models using a variety of immunomodulatory cytokines, including IL-4, IL-2, TNF-alpha, G-CSF, IL-7, IL-6 and GM-CSF, as described in Golumbeck P T et al., Science 254:13-716, 1991; Gansbacher B et al, J. Exp. Med. 172: 1217-1224, 1990; Fearon E R et al., Cell 60:397-403, 1990; Gansbacher B et al., Cancer Res. 50:7820-25, 1990; Teng M et al, PNAS 88:3535-3539, 1991; Columbo M P et al, J. Exp. Med. 174:1291-1298, 1991; Aoki et al., Proc Natl Acad Sci USA. 89(9):3850-4, 1992; Porgador A, et al., Nat Immun. 13(2-3):113-30, 1994; Dranoff G et al., PNAS 90:3539-3543, 1993; Lee C T et al, Human Gene Therapy 8:187-193, 1997; Nagai E et al, Cancer Immunol. Immonther. 47:2-80, 1998 and Chang A et al., Human Gene Therapy 11:839-850, 2000, respectively.

Clinical trials employing GM-CSF-expressing autologous or allogeneic cellular immunotherapies have commenced for treatment of prostate cancer, melanoma, lung cancer, pancreatic cancer, renal cancer, and multiple myeloma (Dummer R., Curr Opin Investig Drugs 2(6):844-8, 2001; Simons J et al, Cancer Res. 15; 59(20):5160-8, 1999; Soiffer R et al., PNAS 95:13141-13146, 1998; Simons J et al., Cancer Res. 15; 57:1537-1546, 1997; Jaffee E et al, J. Clin Oncol. 19:145-156, 2001; and Salgia R et al, J. Clin Oncol. 21:624-630, 2003).

In yet another approach, autologous tumor cells were genetically altered to produce a costimulatory molecule, such as B7-1 or allogeneic histocompatibility antigens (Salvadori et al. Hum. Gene Ther. 6:1299-1306, 1995 and Plaksin et al. Int. J. Cancer 59:796-801, 1994). While the use of genetically modified tumor cells has met with success in treatment of some forms of cancer, there remains a need for improved treatment regimens with greater potency and/or efficacy and fewer side effects than the therapies currently in use.

SUMMARY OF THE INVENTION

The invention provides improved compositions and methods for the treatment of cancer in a mammal, typically a human, by administering a combination of a cytokine-expressing cellular immunotherapy and an antibody that specifically binds to human Programmed Death (PD)-1.

In one aspect of the invention, the cytokine-expressing cellular immunotherapy expresses GM-CSF.

In another aspect of the invention, the cytokine-expressing cellular immunotherapy is rendered proliferation-incompetent by irradiation.

In yet a further aspect of the invention, administration of the combination results in enhanced therapeutic efficacy relative to administration of the cytokine-expressing cellular immunotherapy or the anti-PD-1 antibody alone.

In yet another aspect of the invention, the cytokine-expressing cellular immunotherapy is typically administered subcutaneously, intratumorally, or intradermally. The injection of irradiated GM-CSF-expressing tumor cells results in a local reaction characterized by the infiltration of dendritic cells (DCs), macrophages, and granulocytes.

In another aspect of the invention, the anti-PD-1 antibody may be administered prior to, at the same time as, or following administration of the cytokine-expressing cellular immunotherapy component of the combination. The anti-PD-1 antibody may be administered via parenteral, e.g., subcutaneous, intratumoral, intravenous, intradermal, oral, transmucosal, or rectal administration. While not intending to be bound to a particular theory of operation, it is believed that blockade of PD-1 through the administration of an anti-PD-1 antibody potentiates anti-tumor immunity by negatively modulating the immunoinhibitory effects of PD-1 signaling in activated T-cells, B-cells and myeloid cells.

The invention further provides a combination of cytokine-expressing cells and an anti-PD-1 antibody, wherein the combination comprises cells that are autologous, allogeneic, or bystander cells.

In another aspect of the invention, the autologous, allogeneic, or bystander cell is rendered proliferation-incompetent by irradiation.

The invention further provides compositions and kits comprising cytokine-expressing cellular immunotherapy combinations for use according to the description provided herein.

BRIEF DESCRIPTION OF THE DRAWINGS

FIG. 1A illustrates the anti-tumor T-cell response in an adoptive transfer model in C57BL/6 mice challenged with live B16F10 tumor cells modified to express ovalbumin as a surrogate antigen (B16.ova) and immunized with GM-CSF-secreting B16.ova cells (GM.ova) alone, or in combination with an anti-PD-1 antibody. The number of ovalbumin-specific T-cells in draining lymph nodes (DLN) (top panel) and spleens (bottom panel) were determined by tetramer staining at 3, 7, 10, 14 and 20 days following immunotherapy.

FIG. 1B illustrates the cytolytic activity of T-cells in mice challenged with live B16 tumor cells modified to express ovalbumin as a surrogate antigen (B16.ova) and immnunized with GM-CSF secreting B16.ova cells (GM.ova) alone, or in combination with an anti-PD-1 antibody. Cytolytic activity was determined by assessing the ratio of CSFE-labeled cells in isolated splenocytes following injection of CSFE-labeled non-pulsed and SIINFEKL peptide pulsed syngeneic splenocytes. Cytolytic activity was assessed at 7, 14, 21 and 28 days post immunotherapy.

FIG. 1C illustrates the number of IFNγ-secreting cells per $5\times10^5$ splenocytes isolated from mice challenged with live B16 tumor cells, then immunized with allogeneic GM-CSF-secreting B16F10 cells alone (B16.Kd.GM), or in combination with an anti-PD-1 antibody. Control animals were administered HBSS at the time of immunization. Isolated splenocytes were stimulated with trp2 peptide (top panel) or irradiated B16F10 cells (bottom panel) before being assayed by ELISPOT.

FIG. 2A illustrates the secretion of the pro-inflammatory cytokine tumor necrosis factor-alpha (TNFα) from splenocytes isolated from mice challenged with live tumor cells, then immunized with GM-CSF-secreting B16F10 cells alone (B16.Kd.GM), or in combination with an anti-PD-1 antibody. Splenocytes were stimulated with irradiated B16 cells for 48 hours before assaying for cytokine secretion.

FIG. 2B illustrates the secretion of the pro-inflammatory cytokine interferon-gamma (IFNγ) from splenocytes isolated from mice challenged with live tumor cells, then immunized with GM-CSF-secreting B16F10 cells alone (B16.Kd.GM), or in combination with an anti-PD-1 antibody. Splenocytes were stimulated with irradiated B16 cells for 48 hours before assaying for cytokine secretion.

FIG. 2C illustrates the secretion of the pro-inflammatory cytokine interleukin-5 (IL-5) from splenocytes isolated from mice challenged with live tumor cells, then immunized with GM-CSF-secreting B16F10 cells alone (B16.Kd.GM), or in combination with an anti-PD-1 antibody. Splenocytes were stimulated with irradiated B16 cells for 48 hours before assaying for cytokine secretion.

FIG. 2D illustrates the secretion of the pro-inflammatory cytokine interleukin-6 (IL-6) from splenocytes isolated from mice challenged with live tumor cells, then immunized with GM-CSF-secreting B16F10 cells alone (B16.Kd.GM), or in combination with an anti-PD-1 antibody. Splenocytes were stimulated with irradiated B16 cells for 48 hours before assaying for cytokine secretion.

FIG. 2E illustrates the secretion of the pro-inflammatory cytokine interleukin-10 (IL-10) from splenocytes isolated from mice challenged with live tumor cells, then immunized with GM-CSF-secreting B16F10 cells alone (B16.Kd.GM), or in combination with an anti-PD-1 antibody. Splenocytes were stimulated with irradiated B16 cells for 48 hours before assaying for cytokine secretion.

FIG. 2F illustrates the secretion of the pro-inflammatory cytokine monocyte chemotactic protein (MCP)-1 from splenocytes isolated from mice challenged with live tumor cells, then immunized with GM-CSF-secreting B16F10 cells alone (B16.Kd.GM), or in combination with an anti-PD-1 antibody. Splenocytes were stimulated with irradiated B16 cells for 48 hours before assaying for cytokine secretion.

FIG. 3B illustrates effector CD8 T-cell infiltration into tumors of mice challenged with live tumor cells, then immunized with GM-CSF-secreting B16F10 cells alone (B16.Kd.GM) or with GM-CSF-secreting B16F10 cells in combination with an anti-PD-1 antibody. Shown is the ratio of CD8+/FoxP3+ cells in the tumor at 3 wks post cellular immunotherapy.

FIG. 3C illustrates the kinetics of CD4$^+$ T-cell infiltration into tumor cells (as measured per $1\times10^6$ tumor cells) in mice challenged with live tumor cells, then immunized with GM-CSF-secreting B16F10 cells alone (B16.Kd.GM), or in combination with an anti-PD-1 antibody. CD4$^+$ T-cell counts were determined at 7, 14 and 21 days post cellular immunotherapy.

FIG. 3D illustrates the kinetics of CD8$^+$ T-cell infiltration into tumor cells (as measured per $1\times10^6$ tumor cells) in mice challenged with live tumor cells, then immunized with GM-CSF-secreting B16F10 cells alone (B16.Kd.GM), or in combination with an anti-PD-1 antibody. CD8$^+$ T-cell counts were determined at 7, 14 and 21 days post cellular immunotherapy.

FIG. 3E illustrates the kinetics of CD8$^+$/107a$^+$ T-cell infiltration into tumor cells (as measured per $1\times10^6$ tumor cells) in mice challenged with live tumor cells, then immunized with GM-CSF-secreting B16F10 cells alone (B16.Kd.GM), or in combination with an anti-PD-1 antibody. CD8$^+$/107a$^+$ T-cell counts were determined at 7, 14 and 21 days post cellular immunotherapy.

FIG. 3F illustrates the kinetics of CD8$^+$/IFNγ$^+$ T-cell infiltration into tumor cells (as measured per $1\times10^6$ tumor cells) in mice challenged with live tumor cells, then immunized with GM-CSF-secreting B16F10 cells alone (B16.Kd.GM), or in combination with an anti-PD-1 antibody. CD8$^+$/IFNγ$^+$ T-cell counts were determined at 7, 14 and 21 days post cellular immunotherapy.

FIG. 3G illustrates tumor progression in mice challenged with live tumor cells, then immunized with GM-CSF-secreting B16F10 cells alone (B16.Kd.GM), or in combination with an anti-PD-1 antibody. Tumors from mice (n=5/group) were excised, digested and single cell suspensions from the entire digest were counted by cell counter. Counts were determined at 7, 14 and 21 days post cellular immunotherapy.

FIG. 6A illustrates the percentage of $CD4^+$ T-cells in the spleens of mice treated with GM-CSF-secreting B16F10 cells alone (B16.Kd.GM) or in combination with an anti-PD-1 antibody.

FIG. 6B illustrates the percentage of $CD8^+$ T-cells in the spleens of mice treated with GM-CSF-secreting B16F10 cells alone (B16.Kd.GM) or in combination with an anti-PD-1 antibody.

FIG. 6C illustrates the percentage of $CD11c^+$ T-cells in the spleens of mice treated with GM-CSF-secreting B16F10 cells alone (B16.Kd.GM) or in combination with an anti-PD-1 antibody.

FIG. 6D illustrates the percentage of $DX5^+$ T-cells in the spleens of mice treated with GM-CSF-secreting B16F10 cells alone (B16.Kd.GM) or in combination with an anti-PD-1 antibody.

FIG. 7A illustrates the percentage of memory T-cells ($Ly6C^+/CD69^-$) in the CD4 subpopulation from spleen taken from mice treated with GM-CSF-secreting B16F10 cells alone (B16.Kd.GM) or in combination with an anti-PD-1 antibody.

FIG. 7B illustrates the percentage of memory T-cells ($Ly6C^+/CD69^-$) in the CD8 subpopulation from spleen taken from mice treated with GM-CSF-secreting B16F10 cells alone (B16.Kd.GM) or in combination with an anti-PD-1 antibody.

FIG. 8 illustrates the reversal of anergy and augmentation of a tumor-specific T-cell response in C57BL/6 mice injected with SIINFEKL peptide (to induce anergy in adoptively transferred OT-1 transgenic T-cells) and immunized with GM-CSF-secreting B16.ova cells (GM.ova) alone, or in combination with an anti-PD-1 antibody. The percentage of antigen-specific T-cells in peripheral blood lymphocytes was determined by tetramer staining at 4, 10, 14, 17, 25 and 31 days following adoptive transfer.

DETAILED DESCRIPTION OF THE INVENTION

Figure 3A:
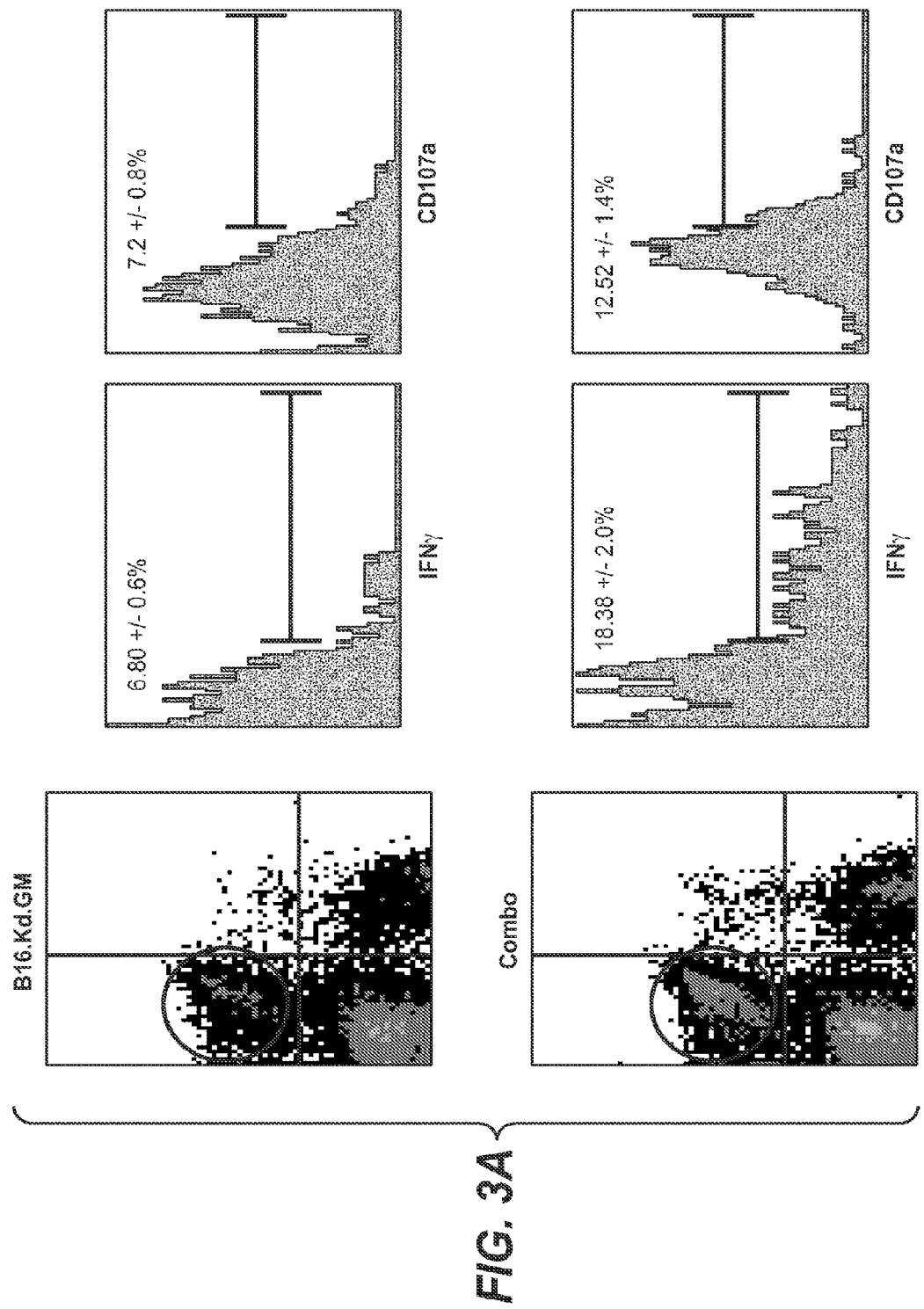
FIG. 3A illustrates effector CD8 T-cell infiltration into tumors of mice challenged with live tumor cells, then immunized with GM-CSF-secreting B16F10 cells alone (B16.Kd.GM) or with GM-CSF-secreting B16F10 cells in combination with an anti-PD-1 antibody (combo). Shown are the percentage of IFNγ and CD107α expressing cells in the CD8 TIL subpopulation.

The present invention represents improved cellular immunotherapies for the treatment of cancer in that the compositions and methods described herein comprise at least two components that act in concert to effect an improved therapeutic outcome for the cancer patient under treatment.

The invention is not limited to the specific compositions and methodology described herein. It is also to be understood that the terminology used herein is for the purpose of describing particular embodiments only, and is not intended to limit the scope of the present invention.

Definitions

The terms "regulating the immune response" or "modulating the immune response" as used herein refers to any alteration in a cell of the immune system or any alteration in the activity of a cell involved in the immune response. Such regulation or modulation includes an increase or decrease in the number of various cell types, an increase or decrease in the activity of these cells, or any other changes which can occur within the immune system. Cells involved in the immune response include, but are not limited to, T lymphocytes, B lymphocytes, natural killer (NK) cells, macrophages, eosinophils, mast cells, dendritic cells and neutrophils. In some cases, "regulating" or "modulating" the immune response means the immune response is stimulated or enhanced, and in other cases "regulating" or "modulating" the immune response means suppression of the immune system. Stimulation of the immune system may include memory responses and/or future protection against subsequent antigen challenge.

The term "cytokine" or "cytokines" as used herein refers to the general class of biological molecules which effect/affect cells of the immune system. The definition is meant to include, but is not limited to, those biological molecules that act locally or may circulate in the blood, and which, when used in the compositions or methods of the present invention serve to regulate or modulate an individual's immune response to cancer. Exemplary cytokines for use in practicing the invention include but are not limited to interferon-alpha (IFN-α), interferon-beta (IFN-β), and interferon-gamma (IFN-γ), interleukins (e.g., IL-1 to IL-29, in particular, IL-2, IL-5, IL-6, IL-7, IL-10, IL-12, IL-15 and IL-18), tumor necrosis factors (e.g., TNF-alpha and TNF-beta), erythropoietin (EPO), MIP3a, monocyte chemotactic protein (MCP)-1, intracellular adhesion molecule (ICAM), macrophage colony stimulating factor (M-CSF), granulocyte colony stimulating factor (G-CSF) and granulocyte-macrophage colony stimulating factor (GM-CSF).

The term "cytokine-expressing cellular immunotherapy" as used herein refers to a composition comprising a population of cells that has been genetically modified to express a cytokine, e.g., GM-CSF, and that is administered to a patient as part of a cancer treatment regimen. The cells of such a "cytokine-expressing cellular immunotherapy" comprise a cytokine-encoding DNA sequence operably linked to expression and control elements such that the cytokine is expressed by the cells. The cells of the "cytokine-expressing cellular immunotherapy" are typically tumor cells and may be autologous or allogeneic to the patient undergoing treatment and or may be "bystander cells" that are mixed with tumor cells taken from the patient. A GM-CSF-expressing "cytokine-expressing cellular immunotherapy" may be referred to herein as "GVAX®".

The term "operably linked" as used herein relative to a recombinant DNA construct or vector means nucleotide components of the recombinant DNA construct or vector are directly linked to one another for operative control of a selected coding sequence. Generally, "operably linked" DNA sequences are contiguous, and, in the case of a secretory leader, contiguous and in reading frame; however, some sequences, e.g., enhancers do not have to be contiguous to be operative and therefore "operably linked."

As used herein, the term "gene" or "coding sequence" means the nucleic acid sequence which is transcribed (DNA) and translated (mRNA) into a polypeptide in vitro or in vivo when operably linked to appropriate regulatory sequences. A "gene" typically comprises the coding sequence plus any non-coding sequences associated with the gene (e.g., regulatory sequences) and hence may or may not include regions preceding and following the coding region, e.g., 5' untranslated (5'UTR) or "leader" sequences and 3' UTR or "trailer" sequences, as well as intervening sequences (introns) between individual coding segments (exons). In contrast, a "coding sequence" does not include non-coding DNA.

The terms "gene-modified" and "genetically-modified" are used herein with reference to a cell or population of cells wherein a nucleic acid sequence has been introduced into the cell or population of cells. The nucleic acid sequence may be heterologous to the cell(s), or it may be an additional copy or altered version of a nucleic acid sequence already present in the cell(s). This term also encompasses cells or a population of cells with altered, e.g., increased or decreased, expression of a nucleic acid sequence endogenous to the cell or population of cells. The cell(s) may be genetically-modified by physical or chemical methods or by the use of recombinant viruses. Chemical and physical methods such as calcium phosphate, electroporation and pressure mediated transfer of genetic material into cells are often used. Several recombinant viral vectors which find utility in effective delivery of genes into mammalian cells include, for example, retroviral vectors, adenovirus vectors, adenovirus-associated vectors (AAV), herpes virus vectors, pox virus vectors. In addition, non-viral means of introduction, for example, naked DNA delivered via liposomes, receptor-mediated delivery, calcium phosphate transfection, electroporation, particle bombardment (gene gun), or pressure-mediated delivery may also be employed to introduce a nucleic acid sequence into a cell or population of cells to render them "gene-modified" or "genetically-modified.

The terms "cancer," "cancer cells," "neoplastic cells," "neoplasia," "tumor," and "tumor cells" (used interchangeably) refer to cells that exhibit relatively autonomous growth, so that they exhibit an aberrant growth phenotype or aberrant cell status characterized by a significant loss of control of cell proliferation. A tumor cell may be a hyperplastic cell, a cell that shows a lack of contact inhibition of growth in vitro or in vivo, a cell that is incapable of metastasis in vivo, or a cell that is capable of metastasis in vivo. Neoplastic cells can be malignant or benign. It follows that cancer cells are considered to have an aberrant cell status.

The term "antigen from a tumor cell" and "tumor antigen" and "tumor cell antigen" may be used interchangeably herein and refer to any protein, carbohydrate or other component derived from or expressed by a tumor cell which is capable of eliciting an immune response. The definition is meant to include, but is not limited to, whole tumor cells that express some or all of the tumor-associated antigens, tumor cell fragments, plasma membranes taken from a tumor cell, proteins purified from the cell surface or membrane of a tumor cell, or unique carbohydrate moieties associated with the cell surface of a tumor cell. The definition also includes those antigens from the surface of the cell which require special treatment of the cells to access.

As described herein, a "tumor cell line" comprises cells that were initially derived from a tumor. Such cells typically are transformed (i.e., exhibit indefinite growth in culture).

The term "systemic immune response" as used herein means an immune response which is not localized, but affects the individual as a whole.

The term "gene therapy" as used herein means the treatment or prevention of cancer by means of ex vivo or in vivo delivery, through viral or non-viral vectors, of compositions containing a recombinant genetic material.

The term "ex vivo" delivery as used herein means the introduction, outside of the body of a human, of compositions containing a genetic material into a cell, tissue, organoid, organ, or the like, followed by the administration of cell, tissue, organoid, organ, or the like which contains such introduced compositions into the body of the same (autologous) or a different (allogeneic) human, without limitation as to the formulation, site or route of administration.

The terms "inactivated cells," "non-dividing cells" and "non-replicating cells" may be used interchangeably herein and refer to cells that have been treated rendering them proliferation incompetent, e.g., by irradiation. Such treatment results in cells that are unable to undergo mitosis, but retain the capability to express proteins such as cytokines or other cancer therapeutic agents. Typically a minimum dose of about 3500 rads is sufficient, although doses up to about 30,000 rads are acceptable. Effective doses include, but are not limited to, 5000 to 10000 rads. Numerous methods of inactivating cells, such as treatment with Mitomycin C, are known in the art. Any method of inactivation which renders cells incapable of cell division, but allows the cells to retain the ability to express proteins may be used in accordance with the present invention.

As used herein "treatment" of an individual or a cell is any type of intervention used in an attempt to alter the natural course of the individual or cell. Treatment includes, but is not limited to, administration of e.g., a cytokine-expressing cellular immunotherapy and at least one additional cancer therapeutic agent or treatment, e.g. an anti-PD-1 antibody, and may be performed either prophylactically or subsequent to diagnosis as part of a primary or follow-up therapeutic regimen.

The term "administering" as used herein refers to the physical introduction of a composition comprising a cytokine-expressing cellular immunotherapy and at least one additional cancer therapeutic agent or treatment to a patient with cancer. Any and all methods of introduction are contemplated according to the invention; the method is not dependent on any particular means of introduction. Means of introduction are well-known to those skilled in the art, examples of which are provided herein.

The term "co-administering" as used herein means a process whereby the combination of a cytokine-expressing cellular immunotherapy and at least one additional cancer therapeutic agent, e.g., an anti-PD-1 antibody, is administered to the same patient. The cytokine-expressing cellular immunotherapy and additional cancer therapeutic may be administered simultaneously, at essentially the same time, or sequentially. If administration takes place sequentially, the cytokine-expressing cellular immunotherapy may be administered before or after a given additional cancer therapeutic agent or treatment. The cytokine-expressing cellular immunotherapy and additional cancer therapeutic agent or treatment need not be administered by means of the same vehicle. The cellular immunotherapy and the additional agent or treatment may be administered one or more times and the number of administrations of each component of the combination may be the same or different. In addition, the cytokine-expressing cellular immunotherapy and additional cancer therapeutic agent or treatment need not be administered at the same site.

The term "therapeutically effective amount" or "therapeutically effective combination" as used herein refers to an amount or dose of a cytokine-expressing cellular immunotherapy together with the amount or dose of an additional agent or treatment, e.g. an anti-PD-1 antibody, that is sufficient to modulate, either by stimulation or suppression, the systemic immune response of an individual. The amount of cytokine-expressing cellular immunotherapy in a given therapeutically effective combination may be different for different individuals and different tumor types, and will be dependent upon the one or more additional agents or treatments included in the combination. The "therapeutically effective amount" is determined using procedures routinely employed by those of skill in the art such that an "improved therapeutic outcome" results.

As used herein, the terms "improved therapeutic outcome" and "enhanced therapeutic efficacy," relative to cancer refers to a slowing or diminution of the growth of cancer cells or a solid tumor, or a reduction in the total number of cancer cells or total tumor burden. An "improved therapeutic outcome" or "enhanced therapeutic efficacy" therefore means there is an improvement in the condition of the patient according to any clinically acceptable criteria, including, for example, decreased tumor size, an increase in time to tumor progression, increased progression-free survival, increased overall survival time, an increase in life expectancy, or an improvement in quality of life. In particular, "improved" or "enhanced" refers to an improvement or enhancement of 1%, 5%, 10%, 25% 50%, 75%, 100%, or greater than 100% of any clinically acceptable indicator of therapeutic outcome or efficacy.

As used herein, the term "synergism," "synergistic" or "synergistically" refers to the combined action of two or more agents wherein the combined action is greater than the sum of the actions of each of the agents used alone.

The term "relative to" or "compared to," when used in the context of comparing the activity and/or efficacy of a combination composition comprising the cytokine-expressing cellular immunotherapy (GVAX) plus an anti-PD-1 antibody (anti-PD-1) to either GVAX or anti-PD-1 alone, refers to a comparison using amounts known to be comparable according to one of skill in the art. Comparable amounts of GVAX, when comparing the combination therapy to GVAX alone, may be based on cell number, cytokine expression, cytokine secretion, or cytokine activity on a per cell basis. Comparable amounts of anti-PD-1, when comparing the combination therapy to PD-1 alone, may be based on equimolar amounts, weight-to-weight equivalents, or units of PD-1 binding activity.

The term "reversal of an established tumor" as used herein means the suppression, regression, partial or complete disappearance of a pre-existing tumor. The definition is meant to include any diminution, for example, in the size, growth rate, appearance or cellular compositions of a preexisting tumor.

The terms "individual" or "subject" as referred to herein is a vertebrate, preferably a mammal, and typically refers to a human.

The terms "programmed death-1," "programmed death receptor-1" and "PD-1" are synonymous with one another, and include variants, isoforms, species homologs of human PD-1, and analogs having at least one common epitope with PD-1. The full length human PD-1 cDNA is 2106 nucleotides long and encodes a protein of 288 amino acid residues. The human PD-1 and murine PD-1 genes share 70% homology at the nucleotide level and 60% homology at the amino acid level. The complete cDNA sequence of human PD-1 has the Genbank accession number U64863 (Shinohara et al., *Genomics* 23(3): 704-706 (1994). The extracellular domain is encoded by amino acids 1-166; the transmembrane domain is encoded by amino acids 167-196; and the cytoplasmic domain is encoded by amino acids 197-288. The extracellular domain contains an immunoglobulin superfamily domain, and the cytoplasmic domain includes an immunoreceptor tyrosine-based inhibitory motif (ITIM). The complete cDNA sequence of murine PD-1 has the Genbank accession number X67914 (Ishida et al., *EMBO J.* 11(11):3887-3895 (1992)).

An intact "antibody" comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with PD-1. The constant regions of the antibodies may mediate the binding of the immunoglobulin to host tissues or factors, including various cells of the immune system (e.g., effector cells) and the first component (C1q) of the classical complement system. The term antibody includes antigen-binding portions of an intact antibody that retain capacity to bind PD-1. Examples of binding include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al. (1988) *Science* 242:423-426; and Huston et al. (1988) *Proc. Natl. Acad. Sci.* USA 85:5879-5883). Such single chain antibodies are included by reference to the term "antibody." Fragments can be prepared by recombinant techniques or enzymatic or chemical cleavage of intact antibodies.

"Conservative substitution" refers to the substitution in a polypeptide of an amino acid with a functionally similar amino acid. The following six groups each contain amino acids that are conservative substitutions for one another:

Alanine (A), Serine (S), and Threonine (T)
Aspartic acid (D) and Glutamic acid (E)
Asparagine (N) and Glutamine (Q)
Arginine (R) and Lysine (K)
Isoleucine (I), Leucine (L), Methionine (M), and Valine (V)
Phenylalanine (F), Tyrosine (Y), and Tryptophan (W).

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids can be found in Tijssen, 1993, *Laboratory Techniques in Biochemistry and Molecular Biology-Hybridization with Nucleic Acid Probes*, part I, chapter 2, "Overview of principles of hybridization and the strategy of nucleic acid probe assays", Elsevier, NY; Sambrook et al., 2001, *Molecular Cloning: A Laboratory Manual*, Cold Spring Harbor Laboratory, 3$^{rd}$ ed., NY; and Ausubel et al., eds., Current Edition, *Current Protocols in Molecular Biology*, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

One example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, *J. Mol. Biol.* 215:403-10 (with special reference to the published default setting, i.e., parameters w=4, t=17) and Altschul et al., 1997, *Nucleic Acids Res.*, 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

Another alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

The term "about," as used herein, unless otherwise indicated, refers to a value that is no more than 10% above or below the value being modified by the term. For example, the term "about 5 µg/kg" means a range of from 4.5 µg/kg to 5.5 µg/kg. As another example, "about 1 hour" means a range of from 54 minutes to 66 minutes.

General Techniques

The practice of the present invention can employ, unless otherwise indicated, conventional techniques of molecular biology, microbiology, cell biology, biochemistry and immunology, which are within the knowledge of those of skill of the art. Such techniques are explained fully in the literature, such as, "Molecular Cloning: A Laboratory Manual", third edition (Sambrook et al., 2002); "Current Protocols in Molecular Biology" (F. M. Ausubel et al., eds., 2007); "Culture of Animal Cells: A Manual of Basic Techniqaue," 4$^{th}$ edition (R. I. Freshney, ed., 2000), each of which is hereby expressly incorporated herein by reference.

Cancer Targets

The methods and compositions of the invention provide an improved therapeutic approach to the treatment of cancer by co-administration of a cytokine-expressing cellular immunotherapy and an antibody that specifically binds to human PD-1 to a patient with cancer. "Cancer" as used herein includes cancer localized in tumors, as well as cancer not localized in tumors, such as, for instance, cancer cells that expand from a local tumor by invasion (i.e., metastasis). The invention finds utility in the treatment of any form of cancer, including, but not limited to, cancer of the bladder, breast, colon, kidney, liver, lung, ovary, cervix, pancreas, rectum, prostate, stomach, epidermis; a hematopoietic tumor of lymphoid or myeloid lineage; a tumor of mesenchymal origin such as a fibrosarcoma or rhabdomyosarcoma; other tumor types such as melanoma, teratocarci-noma, neuroblastoma, glioma, adenocarcinoma and non-small lung cell carcinoma.

Introduction of Cytokine into Cells

In one aspect of the invention, a nucleic acid sequence (i.e., a recombinant DNA construct or vector) encoding a cytokine operably linked to a promoter is introduced into a cell or population of cells. Any and all methods of introduction into a cell or population of cells, typically tumor cells, are contemplated according to the invention. The method is not dependent on any particular means of introduction and is not to be so construed.

The "vector" may be a DNA molecule such as a plasmid, virus or other vehicle, which contains one or more heterologous or recombinant DNA sequences, e.g., a nucleic acid sequence encoding a cytokine under the control of a functional promoter and in some cases further including an enhancer that is capable of functioning as a vector, as understood by those of ordinary skill in the art. An appropriate viral vector includes, but is not limited to, a retrovirus, a lentivirus, an adenovirus (AV), an adeno-associated virus (AAV), a simian virus 40 (SV-40), a bovine papilloma virus, an Epstein-Barr virus, a herpes virus, a vaccinia virus, a Moloney murine leukemia virus, a Harvey murine sarcoma virus, a murine mammary tumor virus, and a Rous sarcoma virus. Non-viral vectors are also included within the scope of the invention.

Any suitable vector can be employed that is appropriate for introduction of nucleic acids into eukaryotic tumor cells, or more particularly animal tumor cells, such as mammalian, e.g., human, tumor cells. Preferably the vector is compatible with the tumor cell, e.g., is capable of imparting expression of the coding sequence for a cytokine and is stably maintained or relatively stably maintained in the tumor cell. Desirably the vector comprises an origin of replication and the vector may or may not also comprise a "marker" or "selectable marker" function by which the vector can be identified and selected. While any selectable marker can be used, selectable markers for use in such expression vectors are generally known in the art and the choice of the proper selectable marker will depend on the host cell. Examples of selectable marker genes which encode proteins that confer resistance to antibiotics or other toxins include ampiciilin, methotrexate, tetracycline, neomycin (Southern and Berg, J., 1982), myco-phenolic acid (Mulligan and Berg, 1980), puromycin, zeo-mycin, hygromycin (Sugden et al., 1985) or G418.

In practicing the methods of the present invention, a vector comprising a nucleic acid sequence encoding a cytokine may be transferred to a cell in vitro, preferably a tumor cell, using any of a number of methods which include but are not limited to electroporation, membrane fusion with liposomes, Lipofectamine treatment, high velocity bombardment with DNA-coated microprojectiles, incubation with calcium phosphate-DNA precipitate, DEAE-dextran mediated transfection, infection with modified viral nucleic acids, direct microinjection into single cells, etc. Procedures for the cloning and expression of modified forms of a native protein using recombinant DNA technology are generally known in the art, as described in Ausubel, et al., 2007 and Sambrook, et al., 2002, expressly incorporated by reference, herein.

Reference to a vector or other DNA sequences as "recombinant" merely acknowledges the operable linkage of DNA sequences which are not typically operably linked as isolated from or found in nature. A "promoter" is a DNA sequence that directs the binding of RNA polymerase and thereby promotes RNA synthesis. "Enhancers" are cis-acting elements that stimulate or inhibit transcription of adjacent genes. An enhancer that inhibits transcription also is termed a "silencer." Enhancers can function (i.e. be operably linked to a coding sequence) in either orientation, over distances of up to several kilobase pairs (kb) from the coding sequence and from a position downstream of a transcribed region. Regulatory (expression/control) sequences are operatively linked to a nucleic acid coding sequence when the expression/control sequences regulate the transcription and, as appropriate, translation of the nucleic acid sequence. Thus, expression/control sequences can include promoters, enhancers, transcription terminators, a start codon (i.e., ATG) in front of the coding sequence, a splicing signal for introns, and stop codons.

Recombinant vectors for the production of cellular immunotherapies of the invention provide the proper transcription, translation and processing signals (e.g., splicing and polyadenylation signals) such that the coding sequence for the cytokine is appropriately transcribed and translated in the tumor cells into which the vector is introduced. The manipulation of such signals to ensure appropriate expression in host cells is within the skill of the ordinary skilled artisan. The coding sequence for the cytokine may be under control of (i.e., operably linked to) its own native promoter, or a non-native (e.g. heterologous) promoter, including a constitutive promoter, e.g., the cytomegalovirus (CMV) immediate early promoter/enhancer, the Rous sarcoma virus long terminal repeat (RSV-LTR) or the SV-40 promoter.

Alternately, a tissue-specific promoter (a promoter that is preferentially activated in a particular type of tissue and results in expression of a gene product in that tissue) can be used in the vector. Such promoters include but are not limited to a liver specific promoter (Ill C R, et al., Blood Coagul Fibrinolysis 8 Suppl 2:S23-30, 1997) and the EF-1 alpha promoter (Kim D W et al. Gene. 91(2):217-23,1990, Guo Z S et al. Gene Ther. 3(9):802-10, 1996; U.S. Pat. Nos. 5,266,491 and 5,225,348, each of which expressly incorporated by reference herein). Inducible promoters also find utility in practicing the methods described herein, such as a promoter containing the tet responsive element (TRE) in the tet-on or tet-off system as described (ClonTech and BASF), the metallothienein promoter which can be upregulated by addition of certain metal salts and rapamycin inducible promoters (Rivera et al., 1996, Nature Med, 2(9): 1028-1032; Ye et al., 2000, Science 283: 88-91; Sawyer T K et al., 2002, Mini Rev Med Chem. 2(5):475-88). Large numbers of suitable tissue-specific or regulatable vectors and promoters for use in practicing the current invention are known to those of skill in the art and many are commercially available.

Exemplary vector systems for use in practicing the invention include the retroviral MFG vector, described in U.S. Pat. No. 5,637,483, expressly incorporated by reference herein. Other useful retroviral vectors include pLJ, pEm and [alpha] SGC, described in U.S. Pat. No. 5,637,483 (in particular Example 12), U.S. Pat. Nos. 6,506,604, 5,955,331 and U.S. Ser. No. 09/612,808, each of which is expressly incorporated by reference herein.

Further exemplary vector systems for use in practicing the invention include second, third and fourth generation lentiviral vectors, U.S. Pat. Nos. 6,428,953, 5,665,577 and 5,981,276 and WO 00/72686, each of which is expressly incorporated by reference herein.

Additional exemplary vector systems for use in practicing the present invention include adenoviral vectors, described for example in U.S. Pat. No. 5,872,005 and International Patent Publication No. WO 00/72686, each of which is expressly incorporated by reference herein.

Yet another vector system that is preferred in practicing the methods described herein is a recombinant adeno-associated vector (rAAV) system, described for example in International Patent Publication Nos. WO 98/46728 and WO 00/72686, Samulski et al., Virol. 63:3822-3828 (1989) and U.S. Pat. Nos. 5,436,146, 5,753,500, 6,037,177, 6,040,183 and 6,093,570, each of which is expressly incorporated by reference herein.

Cytokines

Cytokines and combinations of cytokines have been shown to play an important role in the stimulation of the immune system. The term "cytokine" is understood by those of skill in the art, as referring to any immunopotentiating protein (including a modified protein such as a glycoprotein) that enhances or modifies the immune response to a tumor present in the host. The cytokine typically enhances or modifies the immune response by activating or enhancing the activity of cells of the immune system and is not itself immunogenic to the host.

It follows from the results presented herein that a variety of cytokines will find use in the present invention. Exemplary cytokines for use in practicing the invention include but are not limited to interferon-alpha (IFN-$\alpha$), interferon-beta (IFN-$\beta$), and interferon-gamma (IFN-$\gamma$), interleukins (e.g., IL-1 to IL-29, in particular, IL-2, IL-7, IL-12, IL-15 and IL-18), tumor necrosis factors (e.g., TNF-alpha and TNF-beta), erythropoietin (EPO), MIP3a, intracellular adhesion molecule (ICAM), macrophage colony stimulating factor (M-CSF), granulocyte colony stimulating factor (G-CSF) and granulocyte-macrophage colony stimulating factor (GM-CSF). The cytokine may be from any source, however, optimally the cytokine is of murine or human origin (a native human or murine cytokine) or is a sequence variant of such a cytokine, so long as the cytokine has a sequence with substantial homology to the human form of the cytokine and exhibits a similar activity on the immune system. It follows that cytokines with substantial homology to the human forms of IFN-alpha, IFN-beta, and IFN-gamma, IL-1 to IL-29, TNF-alpha, TNF-beta, EPO, MIP3a, ICAM, M-CSF, G-CSF and GM-CSF are useful in practicing the invention, so long as the homologous form exhibits the same or a similar effect on the immune system. Proteins that are substantially similar to any particular cytokine, but have relatively minor changes in protein sequence find use in the present invention. It is well known that small alterations in protein sequence may not disturb the functional activity of a protein molecule, and thus proteins can be made that function as cytokines in the present invention but differ slightly from current known or native sequences.

Variant Sequences

Homologues and variants of native human or murine cytokines are included within the scope of the invention. As used herein, the term "sequence identity" means nucleic acid or amino acid sequence identity between two or more aligned sequences and is typically expressed as a percentage ("%"). The term "% homology" is used interchangeably herein with the term "% identity" or "% sequence identity" and refers to the level of nucleic acid or amino acid sequence identity between two or more aligned sequences, when aligned using a sequence alignment program. For example, as used herein, 80% homology has the same meaning as 80% sequence identity as determined by a defined algorithm, and accordingly a homologue of a given sequence typically has greater than 80% sequence identity over a length of the given sequence. Preferred levels of sequence identity include, but are not limited to, 80, 85, 88, 89, 90, 91, 92, 93, 94, 95, 96, 97, 98 or 99% or more sequence identity to a native cytokine amino acid or nucleic acid sequence, as described herein.

Exemplary computer programs that can be used to determine the degree of identity between two sequences include, but are not limited to, the suite of BLAST programs, e.g., BLASTN, BLASTX, TBLASTX, BLASTP and TBLASTN, all of which are publicly available on the Internet. See, also, Altschul, S. F. et al. Mol. Biol. 215:403-410, 1990 and Altschul, S. F. et al. Nucleic Acids Res. 25:3389-3402, 1997, expressly incorporated by reference herein. Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. In determining sequence identity, both BLASTN and BLASTX (i.e. version 2.2.5) are run using default parameters of an open gap penalty of 11.0, and an extended gap penalty of 1.0, and utilize the BLOSUM-62 matrix. [See, Altschul, et al., 1997, supra.] A preferred alignment of selected sequences in order to determine "% identity" between two or more sequences, is performed using for example, the CLUSTAL-W program in Mac Vector version 6.5, operated with default parameters, including an open gap penalty of 10.0, an extended gap penalty of 0.1, and a BLOSUM 30 similarity matrix.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about TM-5° C. (5° below the Tm of the probe) "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe, while high stringency conditions are used to identify sequences having about 80% or more sequence identity with the probe. An example of high stringency conditions includes hybridization at about 42° C. in 50% formamide, 5×SSC, 5×Denhardt's solution, 0.5% SDS and 100 fig/ml denatured carrier DNA followed by washing two times in 2×SSC and 0.5% SDS at room temperature and two additional times in 0.1×SSC and 0.5% SDS at 42° C. Moderate and high stringency hybridization conditions are well known in the art. See, for example, Sambrook, et al, 1989, Chapters 9 and 11, and in Ausubel, F. M., et al., 1993, (expressly incorporated by reference herein).

Anti-PD-1 Antibodies

As detailed herein, the present invention is directed to a method of improving an individual's immune response to cancer (e.g., a target cancer antigen or antigens) by co-administering a cytokine-expressing cellular immunotherapy (e.g., GM-CSF) and at an antibody which specifically binds to human Programmed Death (PD)-1 to a patient with cancer.

PD-1 is an immunoinhibitory receptor belonging to the CD28 family (Freeman et al., *J. Exp. Med.* 192: 1027 (2000); Okazaki et al., *Curr. Opin. Immunol.* 14: 779 (2002)) and binds to two ligands, PD-L1 and PD-L2. PD-1 is induced on T-cells, B-cells and myeloid cells in-vitro (Agata et al., *Int. Immunol.* 8:765 (1996)), but is predominantly expressed on previously activated T-cells in vivo (Iwai et al., *Immunol. Lett.* 83:215 (2002)).

Studies indicate that PD-1 plays a critical role in immune responses. Engagement of PD-1 by PD-L1 leads to inhibition of T cell proliferation and cytokine production such as IL-2 and IFN-gamma (Freeman et al., *J. Exp. Med.* 192: 1027 (2000). In addition, PD-1 deficient mice exhibit a breakdown of peripheral tolerance and develop systemic autoimmune disease (Nishimura et al., *Immunity* 11: 141-151 (1999); Nishimura et al., *Science* 291: 319-322 (2001)). Over-expression of PD-L1 has been observed in numerous human cancers, including melanomas and carcinomas of lung, ovary, colon, bladder, breast, cervix, liver, and head and neck, and glioblastoma (Dong et al., *Nat. Med.* 8:793-800 (2002); Brown et al., *J. Immunol.* 170:1257-66 (2003); Strome et al,. *Cancer Res.* 63: 6501 (2003); Wintterle et al., *Cancer Res.* 63:7462-7467 (2003)), and PD-L1/PD-1 interaction has been suggested to play a pivotal role in the immune evasion of tumors from the host immune system (Blank et al. *Cancer Immunol. Immunother.* 54(4):307-14 (2005)). Therefore, blockade of PD-L1/PD-1 interaction, e.g., with an antibody which specifically binds PD-1, serves as one possible mechanism for enhancing anti-tumor immunity.

Exemplary anti-PD-1 antibodies and methods for their use are described by Goldberg et al., *Blood* 110(1):186-192 (2007), Thompson et al., *Clin. Cancer Res.* 13(6):1757-1761 (2007), and Korman et al., International Application No. PCT/JP2006/309606 (publication no. WO 2006/121168 A1), each of which are expressly incorporated by reference herein.

The antibodies for use in the present invention include, but are not limited to, monoclonal antibodies, synthetic antibodies, polyclonal antibodies, multispecific antibodies (including bi-specific antibodies), human antibodies, humanized antibodies, chimeric antibodies, single-chain Fvs (scFv) (including bi-specific scFvs), single chain antibodies, Fab fragments, F(ab') fragments, disulfide-linked Fvs (sdFv), and epitope-binding fragments of any of the above. In particular, antibodies for use in the present invention include immunoglobulin molecules and immunologically active portions of immunoglobulin molecules, i.e., molecules that contain a PD-1 binding site that immunospecifically binds to PD-1. The immunoglobulin molecules for use in the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Preferably, the antibodies for use in the invention are IgG, more preferably, IgG1.

The antibodies for use in the invention may be from any animal origin including birds and mammals (e.g., human, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or from mice or other animals that express antibodies from human genes.

The antibodies for use in the present invention may be monospecific, bispecific, trispecific or of greater multispecificity. Multispecific antibodies may immunospecifically bind to different epitopes of a polypeptide or may immunospecifically bind to both a polypeptide as well a heterologous epitope, such as a heterologous polypeptide or solid support material. See, e.g., International Publication Nos. WO 93/17715, WO 92/08802, WO 91/00360, and WO 92/05793; Tutt, et al., 1991, J. Immunol. 147:60-69; U.S. Pat. Nos. 4,474,893, 4,714,681, 4,925,648, 5,573,920, and 5,601,819; and Kostelny et al., 1992, J. Immunol. 148:1547-1553.

The antibodies for use in the invention include derivatives of the antibodies. Standard techniques known to those of skill in the art can be used to introduce mutations in the nucleotide sequence encoding an antibody to be used with the methods for use in the invention, including, for example, site-directed mutagenesis and PCR-mediated mutagenesis which result in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

The antibodies for use in the present invention include derivatives that are modified, i.e., by the covalent attachment of any type of molecule to the antibody. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, synthesis in the presence of tunicamycin, etc. Additionally, the derivative may contain one or more non-classical amino acids.

The present invention also provides antibodies for use in the invention that comprise a framework region known to those of skill in the art. In certain embodiments, one or more framework regions, preferably, all of the framework regions, of an antibody to be used in the compositions and methods for use in the invention are human. In certain other embodiments for use in the invention, the fragment region of an antibody for use in the invention is humanized. In certain embodiments, the antibody to be used with the methods for use in the invention is a synthetic antibody, a monoclonal antibody, an intrabody, a chimeric antibody, a human antibody, a humanized chimeric antibody, a humanized antibody, a glycosylated antibody, a multispecific antibody, a human antibody, a single-chain antibody, or a bispecific antibody.

In certain embodiments, an antibody for use in the invention has a high binding affinity for PD-1. In specific embodiments, an antibody for use in the invention has an association rate constant or $k_{on}$ rate of about $10^5$ M-1s-1 or more, about $5 \times 10^5$ M-1s-1 or more, about $10^6$ M-1s-1 or more, about $5 \times 10^6$ M-1s-1 or more, about $10^7$ M-1s-1 or more, about $5 \times 10^7$ M-1s-1 or more, about $10^8$ M-1s-1 or more, about $5 \times 10^8$ M-1s-1 or more, or about $1 \times 10^9$ M-1s-1 or more.

In other embodiments, an antibody for use in the invention has a $k_{off}$ rate for PD-1 of about $5 \times 10^{-1}$ s-1 or less, about $10^{-1}$ s-1 or less, about $5 \times 10^{-2}$ s-1 or less, about $10^{-2}$ s-1 or less, about $5 \times 10^{-3}$ s-1 or less, about $10^{-3}$ s-1 or less, about $5 \times 10^{-4}$ s-1 or less, about $10^{-4}$ s-1 or less, about $5 \times 10^{-5}$ s-1 or less, about $10^{-5}$ s-1 or less, about $5 \times 10^{-6}$ s-1 or less, about $10^{-6}$ s-1 or less, about $5 \times 10^{-7}$ s-1 or less, about $10^{-7}$ s-1 or less, about $5 \times 10^{-8}$ s-1 or less, about $10^{-8}$ s-1 or less, about $5 \times 10^{-9}$ s-1 or less, about $10^{-9}$ s-1 or less, about $5 \times 10^{-10}$ s-1 or less, or about $10^{-1}$ s-1 or less.

In certain embodiments, an antibody for use in the invention has an affinity constant or $K_a$ ($k_{on}/k_{off}$) for PD-1 of about $10^2$ M-1 or more, about $5 \times 10^2$ M-1 or more, about $10^3$ M-1 or more, about $5 \times 10^3$ M-1 or more, about $10^4$ M-1 or more, about $5 \times 10^4$ M-1 or more, about $10^5$ M-1 or more, about $5 \times 10^5$ M-1 or more, about $10^6$ M-1 or more, about $5 \times 10^6$ M-1 or more, about $10^7$ M-1 or more, about $5 \times 10^7$ M-1 or more, about $10^8$ M-1 or more, about $5 \times 10^8$ M-1 or more, about $10^9$ M-1 or more, about $5 \times 10^9$ M-1 or more, about $10^{10}$ M-1 or more, about $5 \times 10^{10}$ M-1 or more, about $10^{11}$ M-1 or more, about $5 \times 10^{11}$ M-1 or more, about $10^{12}$ M-1 or more, about $5 \times 10^{12}$ M-1 or more, about $10^{13}$ M-1 or more, about $5 \times 10^{13}$ M-1 or more, about $10^{14}$ M-1 or more, about $5 \times 10^{14}$ M-1 or more, about $10^{15}$ M-1 or more, or about $5 \times 10^{15}$ M-1 or more.

In certain embodiments, an antibody for use in the invention has a low dissociation constant. In specific embodiments, the antibody-binding domain of a carrier construct for use in the invention has a dissociation constant or $K_d$ ($k_{off}/k_{on}$) for antibody about $5 \times 10^{-1}$ M or less, about $10^{-1}$ M or less, about $5 \times 10^{-2}$ M or less, about $10^{-2}$ M or less, about $5 \times 10^{-3}$ M or less, about $10^{-3}$ M or less, about $5 \times 10^{-4}$ M or less, about $10^{-4}$ M or less, about $5 \times 10^{-5}$ M or less, about $10^{-5}$ M or less, about $5 \times 10^{-6}$ M or less, about $10^{-6}$ M or less, about $5 \times 10^{-7}$ M or less, about $10^{-7}$ M or less, about $5 \times 10^{-8}$ M or less, about $10^{-8}$ M or less, about $5 \times 10^{-9}$ M or less, about $10^{-9}$ M or less, about $5 \times 10^{-10}$ M or less, or about $10^{-10}$ M or less.

In certain embodiments, an antibody for use in the present invention has a median effective concentration ($EC_{50}$) of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay. The median effective concentration is the concentration of antibody that neutralizes 50% of PD-1 in an in vitro microneutralization assay.

In certain embodiments, an antibody for use in the invention has a half-life in a subject, preferably a human, of about 12 hours or more, about 1 day or more, about 3 days or more, about 6 days or more, about 10 days or more, about 15 days or more, about 20 days or more, about 25 days or more, about 30 days or more, about 35 days or more, about 40 days or more, about 45 days or more, about 2 months or more, about 3 months or more, about 4 months or more, or about 5 months or more. Antibodies with increased in vivo half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication No. WO 97/34631 and U.S. patent application Ser. No. 10/020,354, entitled "Molecules with Extended Half-Lives, Compositions and Uses Thereof", filed Dec. 12, 2001, by Johnson et al.; and U.S. Publication Nos. 2005/003700 and 2005/0064514, which are incorporated herein by reference in their entireties). Such antibodies can be tested for binding activity to antigens as well as for in vivo efficacy using methods known to those skilled in the art, for example, by immunoassays described herein.

Further, antibodies with increased in vivo half-lives can be generated by attaching to the antibodies polymer molecules such as high molecular weight polyethyleneglycol (PEG). PEG can be attached to the antibodies with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography. PEG-derivatized antibodies can be tested for binding activity to antigens as well as for in vivo efficacy using methods known to those skilled in the art, for example, by immunoassays described herein.

In certain embodiments, an antibody for use in the present invention includes antigen-binding portions of an intact antibody that retain capacity to bind PD-1. Examples include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al. (1988) *Science* 242:423-426; and Huston et al. (1988) *Proc. Natl. Acad. Sci.* USA 85:5879-5883). Such single chain antibodies are included by reference to the term "antibody."

In certain embodiments, the methods of the invention utilize combination immunotherapies that comprise additional molecules that have the capacity to bind PD-1 and/or antagonize PD-1 function. A potential PD-1 antagonist may be a protein closely related to a ligand of PD-1, for example, a mutated form of PD-L1 or PD-L2, that recognizes the PD-1 receptor but imparts no signaling effect, thereby competitively inhibiting the immunoinhibitory action of the ligand. Other potential PD-1 antagonists include small molecules that bind to the receptor binding site or other relevant binding site of PD-1, thereby blocking its normal biological activity. Examples of small molecules include, but are not limited to, small peptides or peptide-like molecules, preferably soluble peptides, and synthetic non-peptidyl organic or inorganic compounds. These small molecules can be identified by screening techniques well known for those skilled in the art.

Other antagonists may include oligonucleotides that bind to PD-1-encoding nucleic acids, such as antisense RNA or DNA constructs prepared using antisense technology, where, e.g., an antisense RNA or DNA molecule acts to block directly the translation of PD-1 mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes a mature tumor antigen herein, is used to design an antisense RNA oligonucleotide of from about 10 to 40 base pairs in length. A DNA oligonucleotide is designed to be complementary to a region of the gene involved in transcription (triple helix-see, Lee et al., Nucl. Acids Res., 6:3073 (1979); Cooney et al., Science, 241: 456 (1988); Dervan et al., Science, 251:1360 (1991)), thereby preventing transcription and the production of the target polypeptide. The antisense RNA oligonucleotide hybridizes to the mRNA in vivo and blocks translation of the mRNA molecule into the target polypeptide (antisense-Okano, Neurochem., 56:560 (1991); Oligodeoxynucleotides as Antisense Inhibitors of Gene Expression (CRC Press: Boca Raton, Fla., 1988).

The oligonucleotides described above can also be delivered to cells such that the antisense RNA or DNA may be expressed in vivo to inhibit production of the PD-1 polypeptide. When antisense DNA is used, oligodeoxyribonucleotides derived from the translation-initiation site, e.g., between about −10 and +10 positions of the target gene nucleotide sequence, are preferred.

Cytokine-Expressing Cellular Immunotherapy

Granulocyte-macrophage colony stimulating factor (GM-CSF) is a cytokine produced by fibroblasts, endothelial cells, T cells and macrophages. This cytokine has been shown to induce the growth of hematopoetic cells of granulocyte and macrophage lineages. In addition, the cytokine activates the antigen processing and presenting function of dendritic cells, which are the major antigen presenting cells (APC) of the immune system. Results from animal model experiments have convincingly shown that GM-CSF producing tumor cells are able to induce an immune response against parental, non-transduced tumor cells.

Autologous and allogeneic cancer cells that have been genetically modified to express a cytokine, e.g., GM-CSF, followed by readministration to a patient for the treatment of cancer are described in U.S. Pat. Nos. 5,637,483, 5,904,920 and 6,350,445, expressly incorporated by reference herein. A form of GM-CSF-expressing genetically modified cancer cells or a "cytokine-expressing cellular immunotherapy" for the treatment of pancreatic cancer is described in U.S. Pat. Nos. 6,033,674 and 5,985,290, expressly incorporated by reference herein. A universal immunomodulatory cytokine-expressing bystander cell line is described in U.S. Pat. No. 6,464,973, expressly incorporated by reference herein. Clinical trials employing GM-CSF-expressing autologous or allogeneic cellular immunotherapies have been undertaken for treatment of prostate cancer, melanoma, lung cancer, pancreatic cancer, renal cancer, and multiple myeloma. A number of these trials are currently ongoing, however, and the question still remains open as to whether the immune response to GM-CSF expressing cells alone will be sufficiently powerful to slow or eradicate large or fast growing malignancies.

The present invention provides an improved method of stimulating an immune response to cancer in a mammalian, preferably a human, subject. Desirably, the method effects a systemic immune response, i.e., a T-cell response and/or a B-cell response, to the cancer. In some embodiments, the method comprises administering to the patient a cytokine-expressing cellular immunotherapy and an antibody that specifically binds to PD-1, wherein the cellular immunotherapy comprises cells which express a cancer antigen or various cancer antigens. The cancer antigen/antigens can be one of the antigens of the cancer found in the patient under treatment. The cells can be rendered proliferation incompetent, such as e.g., by irradiation. Upon administration of the cytokine-expressing cellular immunotherapy and the anti-PD-1 antibody, an immune response to the cancer can be elicited or enhanced.

In one approach, the cytokine expressing cellular immunotherapy comprises a single population of cells that is modified to express a cytokine, e.g. GM-CSF. In another approach, the immunotherapy comprises a single population of cells that is modified to express a cytokine as well as a single chain antibody that specifically binds to PD-1. In another approach, the immunotherapy comprises a combination of two or more populations of cells individually modified to express one component of the immunotherapy, e.g. a cytokine and a single chain anti-PD-1 antibody.

In general, a cytokine-expressing cellular immunotherapy for use in practicing the invention comprises tumor cells selected from the group consisting of autologous tumor cells, allogeneic tumor cells and tumor cell lines (i.e., bystander cells). In one aspect of the invention, the cells of the cytokine-expressing cellular immunotherapy are administered to the same individual from whom they were derived (autologous). In another aspect of the invention, the cells of the cytokine-expressing cellular immunotherapy and the tumor are derived from different individuals (allogeneic or bystander). By way of example, in one approach, genetically modified GM-CSF expressing tumor cells are provided as an allogeneic or bystander cell line and one or more additional cancer therapeutic agents, e.g. an anti-PD-1 antibody, is included in the treatment regimen. In another approach, one or more additional transgenes are expressed by an allogeneic or bystander cell line while a cytokine (i.e., GM-CSF) is expressed by autologous or allogeneic cells, and one or more additional cancer therapeutic agents, e.g. an anti-PD-1 antibody, is included in the treatment regimen.

In a preferred approach, the tumor being treated is selected from the group consisting of cancer of the bladder, breast, colon, kidney, liver, lung, ovary, cervix, pancreas, rectum, prostate, stomach, epidermis, a hematopoietic tumor of lymphoid or myeloid lineage, a tumor of mesenchymal origin such as a fibrosarcoma or rhabdomyosarcoma, melanoma, teratocarcinoma, neuroblastoma, glioma, adenocarcinoma and non-small lung cell carcinoma.

In previous studies, a direct comparison of murine tumor cells transduced with various cytokines demonstrated that GM-CSF-secreting tumor cells induced the best overall antitumor protection. In one preferred embodiment, the cytokine expressed by the cytokine-expressing cellular immunotherapy of the invention is GM-CSF. The preferred coding sequence for GM-CSF is the genomic sequence described in Huebner K. et al, Science 230(4731): 1282-5, 1985. Alternatively the cDNA form of GM-CSF finds utility in practicing the invention (Cantrell et al., Proc. Natl. Acad. Sci., 82, 6250-6254, 1985).

In some embodiments, the cells of the cytokine-expressing cellular immunotherapy are cryopreserved prior to administration. Prior to administration, the cells of a cytokine-expressing cellular immunotherapy of the invention are rendered proliferation incompetent. While a number of means of rendering cells proliferation incompetent are known, irradiation is the preferred method. Preferably, the cytokine-expressing cellular immunotherapy combination is irradiated at a dose of from about 50 to about 200 rads/min, even more preferably, from about 120 to about 140 rads/min prior to administration to the patient. Most importantly, the cells are irradiated with a total radiation dose sufficient to inhibit growth of substantially 100% of the cells, from further proliferation. Thus, desirably the cells are irradiated with a total dose of from about 10,000 to 20,000 rads, optimally, with about 15,000 rads.

Typically more than one administration of cytokine (e.g., GM-CSF) producing cells is delivered to the subject in a course of treatment. Dependent upon the particular course of treatment, multiple injections may be given at a single time point with the treatment repeated at various time intervals. For example, an initial or "priming" treatment may be followed by one or more "booster" treatments. Such "priming" and "booster" treatments are typically delivered by the same route of administration and/or at about the same site. When multiple doses are administered, the first immunization dose may be higher than subsequent immunization doses. For example, a $5 \times 10^6$ prime dose may be followed by several booster doses of $10^6$ to $3 \times 10^6$ GM-CSF producing cells.

A single injection of cytokine-producing cells is typically between about $10^6$ to $10^8$ cells, e.g., $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $10^7$, $2 \times 10^7$, $5 \times 10^7$, or as many as $10^8$ cells. In one embodiment, there are between $10^6$ and $10^8$ cytokine-producing cells per unit dose. The number of cytokine-producing cells may be adjusted according, for example, to the level of cytokine produced by a given cytokine producing cellular immunotherapy.

Autologous

The use of autologous cytokine-expressing cells in a immunotherapy of the invention provides advantages since each patient's tumor expresses a unique set of tumor antigens that can differ from those found on histologically-similar, MHC-matched tumor cells from another patient. See, e.g., Kawakami et al, J. Immunol, 148, 638-643 (1992); Darrow et al., J. Immunol., 142, 3329-3335 (1989); and Horn et al., J. Immunother., 10, 153-164 (1991). In contrast, MHC-matched tumor cells provide the advantage that the patient need not be taken to surgery to obtain a sample of their tumor for immunotherapy production.

In one preferred aspect, the present invention comprises a method of treating cancer by carrying out the steps of: (a) obtaining tumor cells from a mammal, preferably a human, harboring a tumor; (b) modifying the tumor cells to render them capable of producing a cytokine or an increased level of a cytokine naturally produced by the cells relative to unmodified tumor cells; (c) rendering the modified tumor cells proliferation incompetent; and (d) readministering the modified tumor cells to the mammal from which the tumor cells were obtained or to a mammal with the same MHC type as the mammal from which the tumor cells were obtained, in combination with administration of an anti-PD-1 antibody. The administered tumor cells are autologous or MHC-matched to the host.

Allogeneic

Researchers have sought alternatives to autologous and MHC-matched cells as tumor immunotherapies, as reviewed by Jaffee et al., Seminars in Oncology, 22, 81-91 (1995). Early tumor immunotherapy strategies were based on the understanding that the vaccinating tumor cells function as the antigen presenting cells (APCs) and present tumor antigens by way of their MHC class I and II molecules, and directly activate the T cell arm of the immune system. The results of Huang et al. (Science, 264, 961-965, 1994), indicate that professional APCs of the host rather than the vaccinating tumor cells prime the T cell arm of the immune system by secreting cytokine(s) such as GM-CSF such that bone marrow-derived APCs are recruited to the region of the tumor. These results suggest that it may not be necessary or optimal to use autologous or MHC-matched tumor cells in order to elicit an anti-cancer immune response and that the transfer of allogeneic MHC genes (from a genetically dissimilar individual of the same species) can enhance tumor immunogenicity. More specifically, in certain cases, the rejection of tumors expressing allogeneic MHC class I molecules resulted in enhanced systemic immune responses against subsequent challenge with the unmodified parental tumor, as reviewed in Jaffee et al., supra, and Huang et al., supra.

In one preferred aspect, the invention provides a method for treating cancer by carrying out the steps of: (a) obtaining a tumor cell line; (b) modifying the tumor cell line to render the cells capable of producing an increased level of a cytokine relative to the unmodified tumor cell line; (c) rendering the modified tumor cell line proliferation incompetent; and (d) administering the tumor cell line to a mammalian host having at least one tumor that is the same type of tumor as that from which the tumor cell line was obtained or wherein the tumor cell line and host tumor express at least one common antigen, in combination with administration of an anti-PD-1 antibody. The administered tumor cell line is allogeneic and is not MHC-matched to the host. Such allogeneic lines provide the advantage that they can be prepared in advance, characterized, aliquoted in vials containing known numbers of cytokine-expressing cells and stored such that well-characterized cells are available for administration to the patient. Methods for the production of gene-modified allogeneic cells are described for example in International Patent Publication No. WO 00/72686A1, expressly incorporated by reference herein.

In one approach to preparing a cytokine-expressing cellular immunotherapy comprising gene-modified allogeneic cells, cytokine-encoding nucleic acid sequences are introduced into a cell line that is an allogeneic tumor cell line (i.e., derived from an individual other than the individual being treated). The tumor cell line may be of the same type as the tumor or cancer being treated. The tumor and/or tumor cell line may be from any form of cancer, including, but not limited to, carcinoma of the bladder, breast, colon, kidney, liver, lung, ovary, cervix, pancreas, rectum, prostate, stomach, epidermis, a hematopoietic tumor of lymphoid or myeloid lineage, a tumor of mesenchymal origin such as a fibrosarcoma or rhabdomyosarcoma, melanoma, teratocarcinoma, neuroblastoma, glioma, adenocarcinoma, and non-small lung cell carcinoma.

Desirably, the allogeneic cell line expresses GM-CSF in a range from 200-1000 ng/$10^6$ cells/24 h. Preferably, the universal bystander cell line expresses at least about 200 ng GM-CSF/$10^6$ cells/24 hours.

In practicing the invention, one or more allogeneic cell lines can be incubated with an autologous cancer antigen, e.g., an autologous tumor cell (which together comprise an allogeneic cell line composition), then the allogeneic cell line composition can be administered to the patient. Typically, the cancer antigen can be provided by (on) a cell of the cancer to be treated, i.e., an autologous cancer cell. In such cases, the composition can be rendered proliferation-incompetent by irradiation, wherein the allogeneic cells and cancer cells are plated in a tissue culture plate and irradiated at room temperature using a Cs source, as detailed above. The ratio of allogeneic cells to autologous cancer cells in a given administration will vary dependent upon the combination.

Any suitable route of administration can be used to introduce an allogeneic cell line composition into the patient. Preferably, the composition is administered subcutaneously or intratumorally.

The use of allogeneic cell lines in practicing the present invention enables administration of a cytokine-expressing allogeneic cell line to a patient with cancer, together with an autologous cancer antigen. This treatment can result in an effective immune response to a tumor. This approach advantageously obviates the need to culture and transduce autologous tumor cells for each patient, eliminating the problem of variable and inefficient transduction efficiencies.

Bystander

In one further aspect, the present invention provides a universal immunomodulatory cytokine-expressing bystander cell line and an anti-PD-1 antibody. The universal bystander cell line comprises cells which either naturally lack major histocompatibility class I (MHC-I) antigens and major histocompatibility class II (MHC-II) antigens or have been modified so that they lack MHC-I antigens and MHC-II antigens. In one aspect of the invention, a universal bystander cell line is modified by introduction of a vector comprising a nucleic acid sequence encoding a cytokine operably linked to a promoter and expression control sequences necessary for expression thereof. The nucleic acid sequence encoding the cytokine may or may not further comprise a selectable marker sequence operably linked to a promoter. The universal bystander cell line preferably grows in defined, e.g., serum-free, medium, preferably as a suspension.

An example of a preferred universal bystander cell line is K562 (ATCC CCL-243; Lozzio et al, Blood 45(3): 321-334 (1975); Klein et al., Int. J. Cancer 18: 421-431 (1976)). A detailed description of human bystander cell lines is described for example in U.S. Pat. No. 6,464,973 and International Patent Publication No. WO 9938954. Desirably, the universal bystander cell line expresses the cytokine, e.g., GM-CSF in the range from 200-1000 ng/$10^6$ cells/24 h. Preferably, the universal bystander cell line expresses at least about 200 ng GM-CSF/$10^6$ cells/24 hours.

In practicing the invention, the universal bystander cell lines can be incubated with an autologous cancer antigen, e.g., an autologous tumor cell (which together comprise a universal bystander cell line composition), then the universal bystander cell line composition can be administered to the patient. Any suitable route of administration can be used to introduce a universal bystander cell line composition into the patient. Preferably, the composition is administered subcutaneously or intratumorally.

Typically, the cancer antigen can be provided by (on) a cell of the cancer to be treated, i.e., an autologous cancer cell. In such cases, the composition can be rendered proliferation-incompetent by irradiation, wherein the bystander cells and cancer cells are plated in a tissue culture plate and irradiated at room temperature using a Cs source, as detailed above.

The ratio of bystander cells to autologous cancer cells in a given administration will vary dependent upon the combination. With respect to GM-CSF-producing bystander cells, the ratio of bystander cells to autologous cancer cells in a given administration should be such that at least 36 ng GM-CSF/$10^6$ cells/24 hrs is produced, as the therapeutic effect may be decreased if the concentration of GM-CSF is less than this. In addition to the GM-CSF threshold, the ratio of bystander cells to autologous cancer cells should not be greater than 1:1. Appropriate ratios of bystander cells to tumor cells or tumor antigens can be determined using routine methods in the art.

The use of bystander cell lines in practicing the present invention enables administration of a cytokine-expressing bystander cell line to a patient with cancer, together with an autologous cancer antigen. This treatment can result in an effective immune response to a tumor. This approach advantageously obviates the need to culture and transduce autologous tumor cells for each patient, eliminating the problem of variable and inefficient transduction efficiencies.

Evaluation of Combination Immunotherapy in Animal Models

B16F10 Melanoma Model

In one approach, the efficacy of a cytokine-expressing cellular immunotherapy co-administered with an anti-PD-1 antibody can be evaluated by carrying out animal studies in the syngeneic B16F10 melanoma tumor model in the treatment setting. See, e.g., Griswold D P Jr., Cancer Chemother Rep 2; 3(1):315-24, 1972 and Berkelhammer J et al, Cancer Res 42(8):3157-63, 1982. The murine melanoma cell line B16 is a well-defined cell line which is weakly immunogenic in syngeneic C57B16 mice and therefore readily forms tumors in C57BL6 mice. Furthermore, several tumor associated antigens have been identified in this model which allow one to monitor tumor specific as well as antigen specific immune responses. In addition, several murine-specific reagents are commercially available and are used to monitor anti-tumor immune responses in the various immunotherapy strategies. A typical study in the B16F10 melanoma tumor model makes use of at least 6 and generally 10-15 mice per group in order to obtain statistically significant results. Statistical significance can be evaluated using the Student's t-test.

Vaccination of C57BL/6 mice with irradiated GM-CSF-secreting B16F10 tumor cells stimulates potent, long-lasting and specific anti-tumor immunity that prevents tumor growth in most mice subsequently challenged with wild-type B16F10 cells. However, this protection is less effective when GM-CSF-producing tumor cell immunotherapies are administered to mice with preexisting tumor burden. In carrying out studies using the B16F10 melanoma tumor model, female C57BL/6 mice are obtained from Taconic and are 6-8 weeks old at the start of each experiment. In a typical experiment, mice are injected with 1-2×$10^5$ B16BF10 cells on day 0 subcutaneously in a dorsal/anterior location. On day 3, mice are vaccinated in a ventral/posterior location with 1-3×$10^6$ irradiated (10,000 rads) B16F10 or cytokine-expressing cellular immunotherapy. Mice are followed for tumor development and survival. After 14-21 days, mice are sacrificed and their tumor burden assessed by harvesting the mice lungs and counting the surface tumor metastasis and measuring the weight of the lung. An alternative B16F10 melanoma tumor model involves subcutaneous injection of B16F10 tumor cells. A typical in vivo study in the B16F10 melanoma tumor model employs the following groups: HBSS only (negative control); cytokine-expressing cellular immunotherapy/HBSS; (cellular monotherapy control); anti-PD-1 antibody (antibody only control); cytokine-expressing cellular immunotherapy plus anti-PD-1 antibody.

Previous experiments have demonstrated that HBSS or irradiated B16F10 alone do not protect challenged mice from tumor formation. GM-CSF-expressing cellular immunotherapies alone were shown to protect from 10-20% of the challenged mice. The combination of a cytokine-expressing cellular immunotherapy plus an anti-PD-1 antibody is expected to increase the efficacy of anti-tumor protection. The degree of protection depends on several factors, such as the expression level of the cytokine-expressing cellular immunotherapy, the dosage and dosing frequency of the anti-PD-1 antibody, and the relative timing of administration of the anti-PD-1 antibody relative to the timing of administration of the cytokine-expressing cellular immunotherapy.

Immunological Monitoring

Several tumor associated antigens have been identified which allow one to monitor tumor specific as well as antigen-specific immune responses. For example, tumor antigen-specific T cells can be identified by the release of IFN-gamma following antigenic restimulation in vitro (Hu, H-M. et al, Cancer Research, 2002, 62; 3914-3919) (FIGS. 2C, 3B). Yet another example of new methods used to identify tumor antigen-specific T cells is the development of soluble MHC I molecules also known as MHC tetramers (Beckman Coulter, Immunomics), reported to be loaded with specific peptides shown to be involved in an anti-tumor immune response. (FIG. 2A).

Tetramer staining may be used to monitor tumor-specific T-cell responses and to identify very low frequencies of antigen-specific T-cells. Because tetramer staining is performed on freshly isolated lymphocytes within several hours of removal, and without further in vitro stimulation, the technique can be used to estimate the frequency of tumor antigen-specific T-cells in vivo. This provides a means to compare the potency of different tumor immunotherapy strategies.

Examples within the B16F10 melanoma tumor model include but are not limited to gp100, Trp2, Trp-1, and tyrosinase. Similar melanoma-associated antigens have been identified in humans. Such tools provide information that can then be translated into the clinical arena.

Assays for Efficacy of Combination Immunotherapy in In Vivo Models

Tumor burden can be assessed at various time points after tumor challenge using techniques well known in the art. Assays for monitoring anti-tumor response and determining the efficacy of combination immunotherapy are described below. While an improved or enhanced anti-tumor immune response may be most dramatically observed shortly following administration of the immunotherapy, e.g. within 5-10 days, the response may be delayed in some instances, depending on factors such as the expression level of the cytokine-expressing cellular immunotherapy, the dosage and dosing frequency of the anti-PD-1 antibody, and the relative timing of administration of the anti-PD-1 antibody relative to the timing of administration of the cytokine-expressing cellular immunotherapy. Thus, the following assays may be performed on biological samples harvested at much later time points than is indicated below in order to fully assess the anti-tumor response following immunotherapy.

Cytotoxic T lymphocyte (CTL) activity may be determined both in vitro and in vivo. Typically, spleen cells are assessed for CTL activity by in vitro whole cell stimulation for 5 days. Target cells are labeled with $^{51}$Cr and co-incubated with splenic effector CTL, and release of $^{51}$Cr into the supernatants is an indicator of CTL lysis of target cells. On day 3, in vitro stimulated CTL supernatants are tested for IFN-gamma production by CTL. In brief, wells are coated with coating antibody specific for IFN-gamma, supernatant is then added to wells, and IFN-gamma is detected using an IFN-gamma specific detecting antibody. IFN-gamma can also be detected by flow cytometry, in order to measure cell-specific IFN-gamma production.

In vivo CTL activity may be assessed via carboxyfluorescein diacetate succinimidyl ester (CSFE) labeling of syngeneic splenocytes. In brief, splenocyte target populations are evenly split into two populations. The first population is pulsed with antigen specific peptide, e.g. SIINFEKL peptide from OVA, and labeled with a high concentration of CSFE, e.g. 2.5 µM ($CSFE^{hi}$), while the second population is non-pulsed and labeled with a low concentration of CSFE, e.g. 0.25 µM. ($CSFE^{lo}$). An equal number of cells from each population are mixed together and injected into mice immunized with cytokine expressing tumor cell immunotherapy alone, or in combination with anti-PD-1 antibody. 18 hours following injection, splenocytes are harvested and cell suspensions are analyzed by flow cytometry, and cell populations are distinguished based on varying fluorescent intensities. Percent specific lysis is determined by the loss of the peptide-pulsed $CSFE^{hi}$ population compared to the control $CSFE^{lo}$ population. (FIG. 2B).

Another indication of an effective anti-tumor immune response is the production of effector cytokines such as TNF-alpha, IFN-gamma, IL-5, IL-6, IL-10 and monocyte chemotactic protein (MCP)-1 upon restimulation in vitro. Cytokine levels were measured in supernatants from spleen cells restimulated in vitro for 48 hours with irradiated GM-CSF-expressing cells. (FIG. 3)

A further method used to monitor tumor-specific T cell responses is via intracellular cytokine staining (ICS). ICS can be used to monitor tumor-specific T-cell responses and to identify very low frequencies of antigen-specific T-cells. Because ICS is performed on freshly isolated lymphocytes within 5 hours of removal, unlike the CTL and cytokine release assays, which often require 2-7 days of in vitro stimulation, it can be used to estimate the frequency of tumor antigen- specific T-cells in vivo. This provides a powerful technique to compare the potency of different tumor immunotherapy strategies. ICS has been used to monitor T-cell responses to melanoma-associated antigens such as gp 100 and Trp2 following various melanoma immunotherapy strategies. Such T-cells can be identified by the induction of intracellular IFN-gamma expression following stimulation with a tumor-specific peptide bound to MHC I.

Xenogen Imaging of Tumor Models

In some studies, in vivo luminescence of tumor bearing mice is monitored by monitoring of B16F10-luciferase (Xenogen Inc.) injected mice. In brief, Balb/c nu/nu mice are injected with $5\times10^4$ or $2\times10^5$ cells of B16F10-luc cells via tail vein on day 0. Mice are monitored for tumor burden when necessary by intra-peritoneal injection of excess luciferin substrate at 1.5 mg/g mice weight. In a typical analysis, twenty minutes after substrate injection, mice are anesthetized and monitored for in vivo luminescence with Xenogen IVIS Imaging System (Xenogen Inc.) luminescence sensitive CCD camera by dorsal or ventral position. Data is collected and analyzed by Living Image 2.11 software.

Cytokine-Expressing Cellular Immunotherapies Plus Anti-PD-1 Antibodies

Previous reports indicate that GM-CSF-secreting tumor cell immunotherapy provides partial protection of mice when used as a monotherapy for non-immunogenic tumors such as B16 melanoma. The results presented herein demonstrate that the combination of GM-CSF-secreting B16 tumor cells and an anti-PD-1 antibody can act synergistically, resulting in highly protective antitumor immune responses. In order to achieve the maximal synergistic effect of these two agents in clinical trials, possible treatment regimens should be carefully evaluated in preclinical studies. In ongoing clinical trials GM-CSF-secreting tumor cell immunotherapies or anti-PD-1 antibodies are administered to patients repeatedly over a period of several months. In studies described herein, the efficacy of the combination was evaluated in preclinical studies following repeated administration of both GM-CSF-secreting tumor cell immunotherapies and anti-PD-1 antibodies. Example 4 details studies where a cytokine expressing cellular immunotherapy was tested in both a B16F10 and CT26 tumor model with and without co-administration of an anti-PD-1 antibody. The GM-CSF-secreting tumor cell immunotherapy was less effective than the combination therapy of anti-PD-1 antibody and GM-CSF-secreting tumor cell immunotherapies (FIGS. 4, 5).

These results demonstrate that in practicing the present invention, an autologous, allogeneic, or bystander cytokine-expressing cellular immunotherapy may be administered to a cancer patient in combination with an anti-PD-1 antibody, resulting in enhanced therapeutic efficacy and prolonged survival relative to either monotherapy alone.

In a preferred aspect of the methods described herein, a cytokine-expressing cellular immunotherapy is administered in combination with an anti-PD-1 antibody to a cancer patient, wherein the cytokine-expressing cellular immunotherapy comprises mammalian, preferably human tumor cells, and the cells in the cytokine-expressing cellular immunotherapy are rendered proliferation incompetent, such as by irradiation. Administration of a cytokine-expressing cellular immunotherapy in combination with an anti-PD-1 antibody results in an enhanced immune response to the cancer as compared to the immune response to the same cancer following administration of the cytokine-expressing cellular immunotherapy or anti-PD-1 antibody alone.

The cytokine-expressing cellular immunotherapy combination may be administered by any suitable route. Preferably, the composition is administered subcutaneously or intratumorally. Local or systemic delivery can be accomplished by administration comprising administration of the combination into body cavities, by parenteral introduction, comprising intramuscular, intravenous, intraportal, intrahepatic, peritoneal, subcutaneous, or intradermal administration. In the event that the tumor is in the central nervous system, the composition is administered in the periphery to prime naive T-cells in the draining lymph nodes. The activated tumor-specific T-cells are able to cross the blood/brain barrier to find their targets within the central nervous system.

In some embodiments of the combination immunotherapy described herein, the cells of the cytokine-expressing cellular immunotherapy and the anti-PD-1 antibody can be administered at essentially the same time, i.e., concurrently, e.g., within the same hour or same day, etc., or at separately staggered times, i.e. sequentially prior to or subsequent to the administration of the second agent of the combination immunotherapy, e.g., on separate days, weeks, etc. The instant methods are therefore to be understood to include all such regimes of simultaneous or non-simultaneous treatment. In some embodiments, the cells of the cytokine-expressing cellular immunotherapy are administered within 0.1, 0.5, 1, 2, 3, 4, 5, 6, 7, 8, 9, 10, 11, 12, 13, 14, 15, 16, 17, 18 or more than 18 hours of administration of the anti-PD-1 antibody. In some embodiments, the cells of the cytokine-expressing cellular immunotherapy are administered within 1, 2, 3, 4, 5, 6, 7, 8, 9, 10, 11, 12, 13, 14 or more than 14 days of administration of the anti-PD-1 antibody. In some embodiments, the cells of the cytokine-expressing cellular immunotherapy are administered within 1, 2, 3, 4, 5 or more than 5 weeks of administration of the anti-PD-1 antibody.

In some embodiments of the combination immunotherapy described herein, the cells of the cytokine-expressing cellular immunotherapy are administered simultaneously with administration of the anti-PD-1 antibody, for example, with the first administration of the combination therapy and with subsequent administrations of the combination therapy. In a particular embodiment, the cells of the cytokine-expressing cellular immunotherapy are administered simultaneously with the first administration of the anti-PD-1 antibody, and the cells of the cytokine-expressing cellular immunotherapy are administered simultaneously with administration of the anti-PD-1 antibody on a biweekly basis thereafter. In another particular embodiment, the cells of the cytokine-expressing cellular immunotherapy are administered within 0.1, 0.5, 1, 2, 3, 4, 5, 6, 7, 8, 9, 10, 11, 12, 13, 14, 15, 16, 17, 18, 19, 20, 21, 22, 23 or 24 hours of administration of the anti-PD-1 antibody, and the cells of the cytokine-expressing cellular immunotherapy are administered within 0.1, 0.5, 1, 2, 3, 4, 5, 6, 7, 8, 9, 10, 11, 12, 13, 14, 15, 16, 17, 18, 19, 20, 21, 22, 23 or 24 hours of administration of the anti-PD-1 antibody, on a biweekly basis thereafter.

In certain embodiments, cells of the cytokine-expressing cellular immunotherapy are administered prior to administration of the anti-PD-1 antibody. In some embodiments, the cells of the cytokine-expressing cellular immunotherapy are administered one, two, three, four, five, six, seven, or more days prior to administration of the anti-PD-1 antibody. In other embodiments, cells of the cytokine-expressing cellular immunotherapy are administered after administration of the anti-PD-1 antibody. In some embodiments, the cells of the cytokine-expressing cellular immunotherapy are administered one, two, three, four, five, six, seven, or more days after administration of the anti-PD-1 antibody.

As will be understood by those of skill in the art, the optimal treatment regimen will vary. As a result, it will be understood that the status of the cancer patient and the general health of the patient prior to, during, and following administration of a cytokine-expressing cellular immunotherapy in combination with an anti-PD-1 antibody, the patient will be evaluated in order to determine if the dose of each component and relative timing of administration should be optimized to enhance efficacy or additional cycles of administration are indicated. Such evaluation is typically carried out using tests employed by those of skill in the art to evaluate traditional cancer chemotherapy, as further described below in the section entitled "Monitoring Treatment."

Monitoring Treatment

One skilled in the art is aware of means to monitor the therapeutic outcome and/or the systemic immune response upon administering a combination treatment of the present invention. In particular, the therapeutic outcome can be assessed by monitoring attenuation of tumor growth and/or tumor regression and or the level of tumor specific markers. The attenuation of tumor growth or tumor regression in response to treatment can be monitored using one or more of several end-points known to those skilled in the art including, for instance, number of tumors, tumor mass or size, or reduction/prevention of metastasis.

Kits

The combination immunotherapy composition can be included in a kit, container, pack, or dispenser together with instructions for administration. When the composition is supplied as a kit, the different components of the composition may be packaged in separate containers so as to permit long-term storage without losing the active components' functions. The reagents included in the kits can be supplied in containers of any sort such that the life of the different components are preserved, and are not adsorbed or altered by the materials of the container. For example, cytokine-expressing cells may be housed in containers such as test tubes, vials, flasks, bottles, syringes, or the like. Sealed glass ampules may be used to contain lyophilized anti-PD-1 antibody that has been packaged under a neutral, non-reacting gas, such as nitrogen. Ampoules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail.

EXAMPLE 1

Immune Response Following Vaccination with a GM-CSF-Secreting Immunotherapy Combined with Administration of Anti-PD-1 Antibody Immune responses were measured as increases in tumor antigen-specific T-cells. Such T-cells can be identified by immunological monitoring methods, as described above, including (A) tetramer staining, (B) in vivo CTL activity, and (C) the induction of intracellular IFN-gamma expression following stimulation with a tumor-specific peptide or tumor cells.

FIG. 1A illustrates the anti-tumor T-cell response induced by administration of GM-CSF-secreting B16F10 cells alone and in combination with an anti-PD-1 antibody, as determined by tetramer staining On day 0, $1 \times 10^6$ OT-1 transgenic T-cells were adoptively transferred into tumor-bearing C57BL/6 mice which were challenged on day −1 with $2 \times 10^5$ live B16 cells transduced with the surrogate antigen, ovalbumin (F10.ova). On day 3, mice were immunized with $1 \times 10^6$ irradiated GM-CSF-secreting B16 cells expressing ovalbumin as a surrogate antigen (GM.ova) as immunotherapy alone, or immunotherapy was followed by 200 μg and 100 μg of anti-PD-1 antibody on days 3 and 4, respectively, as combination therapy. At the indicated timepoints, draining lymph nodes (top panel) and spleens (bottom panel) were harvested from selected mice (n=5/group) and evaluated for antigen-specific T-cell count by tetramer staining. Immunization with GM.ova plus anti-PD-1 antibody resulted in an increase in the number of antigen specific T-cells in both draining lymph nodes (DLN) and spleen compared to immunization with GM.ova immunotherapy alone. This increase was observed starting at 7 days post immunotherapy and was sustained out to 20 days.

FIG. 1B illustrates the in vivo cytolytic activity of T-cells in mice treated with GM-CSF-secreting B16F10 cells alone and in combination with an anti-PD-1 antibody. On day 0, mice were inoculated with $2 \times 10^5$ live B16F10 cells transduced with the surrogate antigen, ovalbumin (F10.ova). On day 3 mice were immunized with $1 \times 10^6$ irradiated GM-CSF-secreting F10.ova cells (GM.ova) as immunotherapy alone, or immunotherapy was followed by 200 μg and 100 μg of anti-PD-1 antibody on days 3 and 4, respectively, as combination therapy. At the indicated timepoints, mice (n=5/group) were injected with CSFE-labeled non-pulsed and SIINFEKL pulsed syngeneic splenocytes. 18 hrs later, splenocytes were harvested and evaluated for cytolytic activity by measuring the ratio of CSFE-labeled cells. Immunization with cytokine expressing tumor cells alone as well as in combination with anti-PD-1 administration resulted in significant CTL activity at 7 days post immunotherapy. By 21 days post immunotherapy, however, CTL activity was significantly higher (~60% lysis) following combination immunotherapy compared to immunization with cytokine expressing tumor cells alone (<20% lysis). Increased CTL activity was sustained out to 28 days post immunotherapy.

FIG. 1C illustrates the anti-tumor T-cell response induced by administration of GM-CSF-secreting B16F10 cells alone and in combination with an anti-PD-1 antibody, measured as an increase in IFNγ-secretion. On day 0, mice were inoculated subcutaneously with live B16F10 cells. On day 3, $1 \times 10^6$ irradiated GM-CSF-secreting B16F10 cells (B16.Kd.GM) were injected as immunotherapy alone, or immunotherapy was followed by 200 μg and 100 μg of anti-PD-1 antibody on days 3 and 4, respectively, as combination therapy. On day 17, spleens (n=5/group) were removed and an ELISPOT assay was performed to evaluate the number of IFNγ-secreting cells/$5 \times 10^5$ splenocytes when stimulated with the B16-specific Kb peptide, Trp2 (top panel); or irradiated B16F10 (F10; bottom panel). The number of IFNγ-secreting cells was significantly higher in splenocytes from mice receiving combination immunotherapy compared to those receiving GM-CSF expressing tumor cell immunotherapy alone (B16.Kd.GM) following stimulation either trp2 or irradiated B16F10 cells.

Taken together, these results demonstrate that anti-PD-1 antibody augments the anti-tumor T-cell response induced by GM-CSF expressing tumor cell immunotherapy, and support the utility of GM-CSF-secreting tumor cell and anti-PD-1 antibody combination immunotherapy for the induction and/or enhancement of anti-tumor immunity.

EXAMPLE 2

Pro-Inflammatory Cytokine Secretion Following GVAX/anti-PD-1 Combination Immunotherapy A further suggestion as to the potential utility of the combination of GM-CSF-secreting immunotherapies and anti-PD-1 antibody in eliciting an anti-tumor immune response is the production of pro-inflammatory cytokines such as TNF-alpha, IFN-gamma, IL-2, IL-5, IL-6, IL-10 and MCP-1 upon restimulation in vitro. Release of such cytokines is often used as a surrogate marker for monitoring tumor-specific immune responses following immunotherapeutic strategies designed to induce anti-tumor immunity.

FIG. 2 illustrates the secretion of pro-inflammatory cytokines following administration of GM-CSF-secreting B16F10 cells alone and in combination with an anti-PD-1 antibody. On day 0, mice were inoculated subcutaneously with live B16F10 cells. On day 3, mice were immunized with $1\times10^6$ irradiated GM-CSF-secreting B16F10 cells (B16.Kd.GM) as immunotherapy alone, or immunotherapy was followed by 200 µg and 100 µg of anti-PD-1 antibody on days 3 and 4, respectively, as combination therapy. On day 17, splenocytes from selected mice (n=5/group) were cultured with irradiated B16 cells for 48 hrs in 96 well plates. Supernatants were evaluated for secretion levels of the following cytokines: (A) tumor necrosis factor-alpha (TNFα), (B) interferon-gamma (IFNγ), (C) interleukin-5 (IL-5), (D) interleukin-6 (IL-6), (E) interleukin-10 (IL-10), and (F) monocyte chemotactic protein (MCP)-1.

For each cytokine assayed, cytokine secretion was significantly higher in splenocytes from mice receiving combination immunotherapy compared to those receiving GM-CSF expressing tumor cell immunotherapy alone. Thus, these results further support the utility of GM-CSF-secreting tumor cell immunotherapy and anti-PD-1 antibody combination immunotherapy for the induction and/or enhancement of anti-tumor immunity.

EXAMPLE 3

Recruitment of T-cells into Tumors Following GVAX/anti-PD-1 Combination Immunotherapy FIG. 3 illustrates effector CD8 T-cell infiltration into tumors in mice treated with GM-CSF-secreting B16F10 cells alone or in combination with an anti-PD-1 antibody. High numbers of tumor infiltrating lymphocytes (TIL) within tumors have been shown to correlate with overall therapeutic benefit (Dunn et al., *Nat Immunol*. 3(11):991-8., 39 (2002); Smyth et al., *Nat Immunol*. 2(4):293-9 (2001). Thus, the extent of infiltrating lymphocytes in tumors of B16.Kd.GM-treated animals compared to animals treated with the combination therapy was examined. On day 0, mice were inoculated subcutaneously with live B16F10 cells. On day 3, $1\times10^6$ irradiated GM-CSF-secreting B16F10 cells (B16.Kd.GM) were injected as immunotherapy alone, or with 200 µg and 100 µg of anti-PD-1 antibody on days 3 and 4, respectively, as combination therapy. At the indicated timepoints, tumors from mice were excised, digested and stained, and single cell suspensions were evaluated by flow cytometry. FIG. 3 shows the percentage of IFNγ and CD107α expressing cells in the CD8 tumor infiltrating lymphocyte (TIL) subpopulation from mice immunized with (A) GM-CSF expressing tumor cell immunotherapy alone, and GM-CSF expressing tumor cell immunotherapy alone plus anti-PD-1 antibody. Also shown is the ratio of CD8+/FoxP3+ cells in the tumor at 3 wks post cellular immunotherapy (B). Also shown are the kinetics of (C) CD4+ T-cells, (D) CD8+ T-cells, (E) CD8+ and CD107α+ T-cells, and (F) CD8+ and IFNγ+ T-cells per $1\times10^6$ tumor cells. Tumor progression for these animals is shown in (G).

CD4/IFN-γ co-staining was used to identify effector CD4 T-cells and CD8/IFN-γ or CD8/CD107a co-staining was used to identify effector CD8 T-cells within tumors. IFN-γ secreted by T-cells has previously been shown to correlate with immunoregulatory and anti-tumor properties (Schroder et al., *J. Leukoc. Biol*. 75(2):163-89 (2004), while expression of CD107a is associated with cytolytic activity of T-cells (Betts et al., *J. Immunol. Methods* 281(1-2):65-78, (2003); and Rubio et al., *Nat Med*. 9(11):1377-82 (2003)). Animals receiving the combination therapy showed an increased in the percentage of activated CD8 effector T-cells within tumors compared to animals that received B16.Kd.GM monotherapy (FIG. 3A). Furthermore, HBSS control animals had minimal CD4 and CD8 T-cell infiltration into tumors, correlating with tumor progression of these animals (FIGS. 3C-D and 3G). Comparatively, animals treated with B16.Kd.GM monotherapy displayed gradual infiltration of T-cells into the tumor environment with peak infiltration seen on day 14, which correlated with the delay in tumor growth observed in this group (*p<0.05 HBSS vs. B16.Kd.GM for all time points). Animals treated with the combination therapy exhibited a rapid and persistent tumor infiltration of functional CD4 and CD8 T-cells (*p<0.05 B16.Kd.GM vs. combination therapy on day 21) that correlated with its increased anti-tumor efficacy.

A favorable intratumoral ratio of effector T-cells (Teff) to regulatory T-cells (Treg) post immunotherapy has been described to correlate with overall anti-tumor activity (Quezada et al., *J Clin Invest*. 16(7):1935-45 (2006)) and was therefore assessed in tumors of animals treated with either B16.Kd.GM monotherapy or the combination therapy. At the early time points (week 1 and 2 post immunotherapy), the intratumoral ratio of Teff to Tregs was comparable between B16.Kd.GM monotherapy and the combination therapy treatment groups (data not shown). In contrast, 3 weeks post immunotherapy, the ratio of Teff to Treg was significantly increased in animals that received the combination therapy when compared to B16.Kd.GM immunotherapy-treated animals (FIG. 3B). The correlation between the improved Teff to Treg ratio observed in animals treated with the combination therapy and the better control of tumor growth in this group again suggests that the presence of Tregs in tumors blunts CD8 T-cell activity and that cancer immunotherapies that shift this ratio in favor of the T effector cells are more effective at providing anti-tumor responses. In summary, these data demonstrated a strict correlation between the potency of the anti-tumor T-cell responses measured in the periphery, the number of effector T-cells infiltrating into the tumors and the overall control of disease progression in animals treated with either B16.Kd.GM monotherapy or in combination with an anti-PD-1 antibody.

EXAMPLE 4

Efficacy of Cytokine-Expressing Cellular Immunotherapy Plus Anti-PD-1 Antibody

In vivo studies were carried out using allogeneic B16F10 and autologous CT26 tumor models to determine if an anti-PD-1 antibody in combination with a cytokine-expressing cellular immunotherapy can enhance anti-tumor efficacy compared to immunotherapy alone.

For studies utilizing the B16F10 model, mice were inoculated subcutaneously with $2\times10^5$ live tumor cells on day 0. Mice were then injected with $1\times10^6$ irradiated GM-CSF-secreting B16F10 cells (B16.Kd.GM) as immunotherapy alone, or as combination therapy with 200 µg of anti-PD-1, followed by 100 µg of anti-PD-1 on the following day. Therapy was started at 3 days, 7 days and 11 days following inoculation to assess the effect of delayed administration on efficacy. Mice were monitored for the formation of palpable tumors twice weekly. Mice were assessed daily for any obvious abnormality, and if subcutaneous tumors reached 15-20 mm-diameter in size or started to ulcerate through the skin, animals were euthanized. A Kaplan-Meier survival curve was used for evaluation. Survival curves are shown for mice treated with immunotherapy at 3 days (FIG. 4A), 7 days (FIG. 4B), or 11 days (FIG. 4C) post inoculation.

Figure 4A:
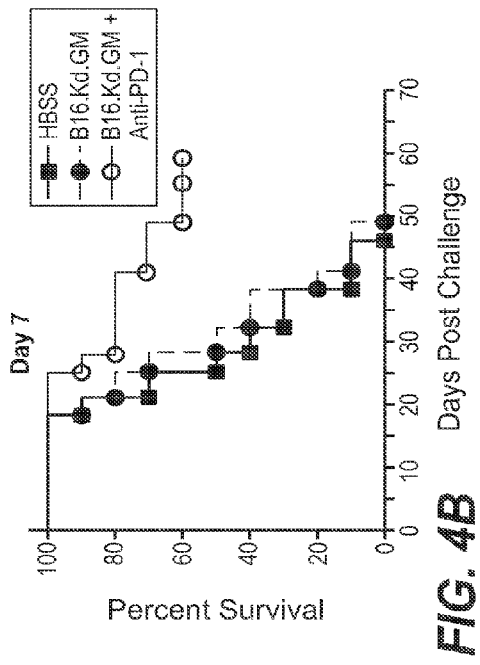
FIG. 4A illustrates the survival of B16F10 tumor-bearing animals following administration of GM-CSF-secreting B16F10 cells alone (B16.Kd.GM) or in combination with an anti-PD-1 antibody, when given on day 3 post tumor challenge.
Figure 4B:
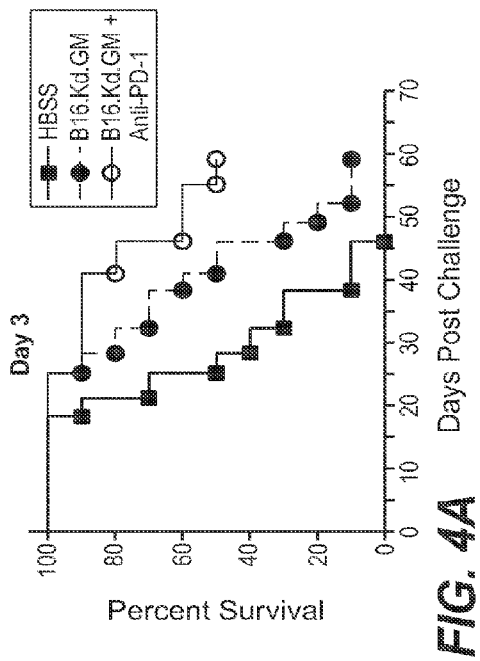
FIG. 4B illustrates the survival of B16F10 tumor-bearing animals following administration of GM-CSF-secreting B16F10 cells alone (B16.Kd.GM) or in combination with an anti-PD-1 antibody, when given on day 7 post tumor challenge.
Figure 4C:
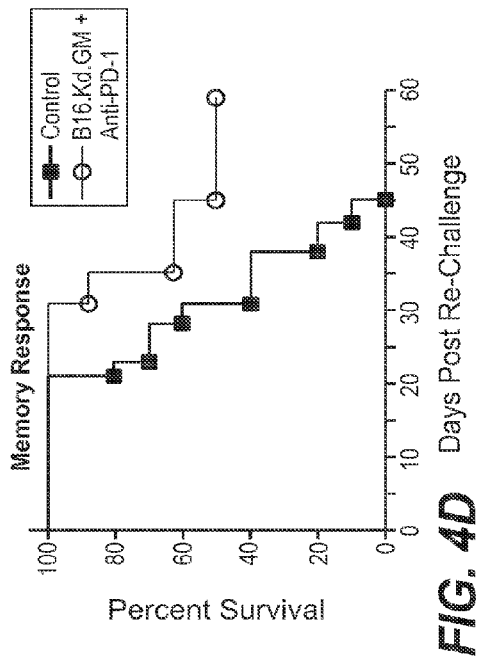
FIG. 4C illustrates the survival of B16F10 tumor-bearing animals following administration of GM-CSF-secreting cells alone (B16.Kd.GM) or in combination with an anti-PD-1 antibody, when given on day 11 post tumor challenge.
Figure 4D:
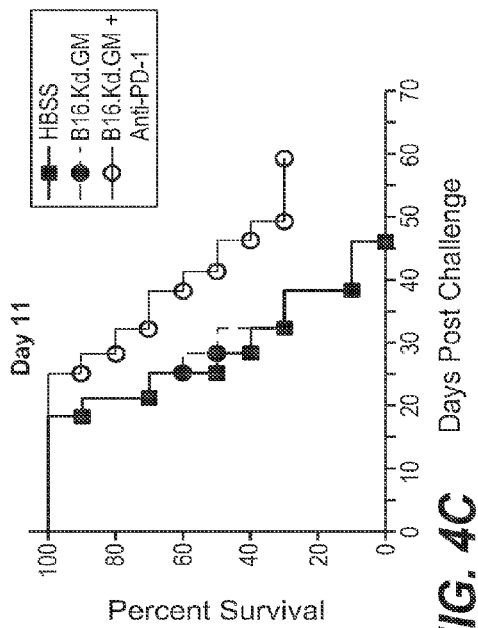
FIG. 4D illustrates the memory response of mice which survived an initial tumor challenge following administration of GM-CSF-secreting cells alone or in combination with an anti-PD-1 antibody. On day 90 after initial tumor challenge, animals were re-challenged with $5 \times 10^5$ (2.5 fold of initial dose) B16 tumor cells and monitored for survival. A Kaplan-Meier survival curve was used for evaluation.

For each dosing regimen, survival was significantly enhanced in mice treated with the combination therapy compared to immunotherapy alone. HBSS-injected control animals had a MST of 26 days and animals treated with B16.Kd.GM immunotherapy on day 3 had a MST of 44 days with 10% long-term survival (*p=0.01 HBSS vs. B16.Kd.GM). MST was further prolonged to 57 days in animals that were treated with the combination therapy on day 3 with 50% long-term survival (*p<0.05 B16.Kd.GM+anti-PD-1 vs. B16.Kd.GM) (FIG. 4A). MSTs were 30 days when B16.Kd.GM immunotherapy was delayed to either day 7 or day 11 post-tumor challenge and all animals succumbed to tumor burden by day 45-50. Again, enhanced anti-tumor activity was observed in animals that received the combination therapy initiated either on day 7 or day 11, with 60% (MST=not reached) and 30% (MST=42 days) of animals surviving long-term, respectively (day 7 initiation of therapy *p<0.005 or day 11 initiation of therapy *p=0.01, long-term survival of B16.Kd.GM+anti-PD-1 vs. B16.Kd.GM) (FIGS. 4B and 4C). Furthermore, on day 90, re-challenge of surviving mice on day 90 in both immunotherapy alone and combination therapy groups with 2.5-times the initial dose of live tumor cells demonstrated the presence of a potent B16-specific memory response, suggesting that the induction of memory responses is B16.Kd.GM dependent (FIG. 4D). Thus, the combination of GM-CSF-secreting tumor cell immunotherapy and anti-PD-1 antibody is potent enough to significantly delay tumor growth of well established primary tumors and to maintain memory responses for protection against tumor re-occurrence.

To evaluate the potency of this combination therapy in a second model, the in vivo study was repeated in the autologous immunogenic CT26 colon carcinoma tumor model in Balb/c animals. In this study, mice were inoculated subcutaneously with $2 \times 10^5$ live tumor cells on day 0. On day 3, mice were then injected with wither $1 \times 10^6$ irradiated GM-CSF-secreting CT26 cells (CT26.GM) as immunotherapy alone or as combination therapy with 200 μg of anti-PD-1, followed by 100 μg of anti-PD-1 on day 4. Anti-PD-1 antibody alone was also administered as a control, at 200 μg on day 3 post challenge followed by 100 μg anti-PD-1 on day 4.

Figure 5A:
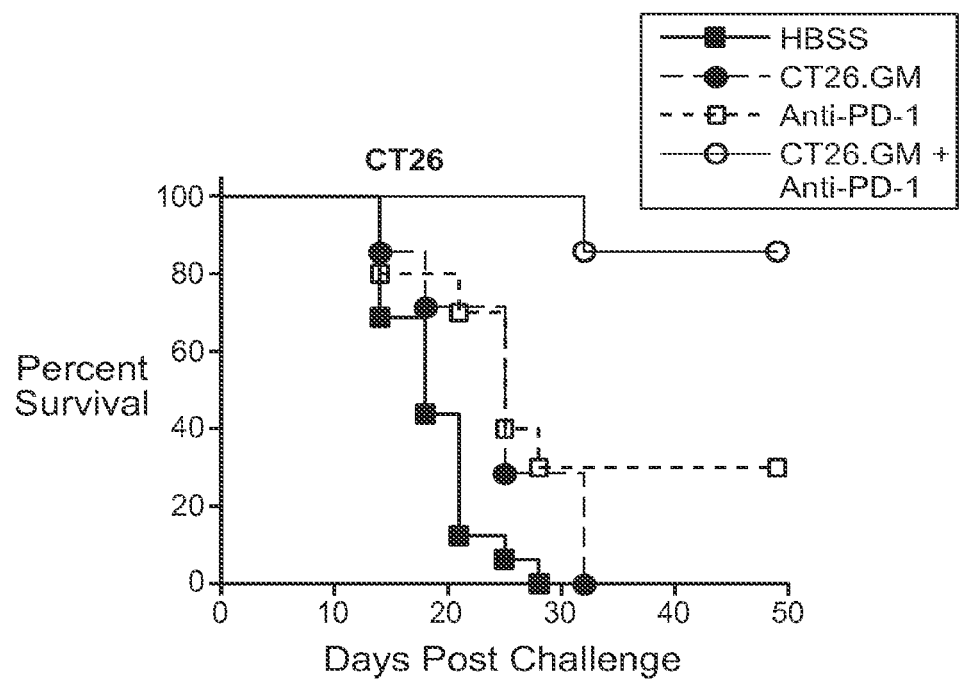
FIG. 5A illustrates the survival of CT26 tumor-bearing animals following administration of GM-CSF-secreting CT26 cells alone (CT26.GM), anti-PD-1 antibody alone (anti-PD-1) or CT26.GM in combination with an anti-PD-1 antibody when given on day 3 post tumor challenge.
Figure 5B:
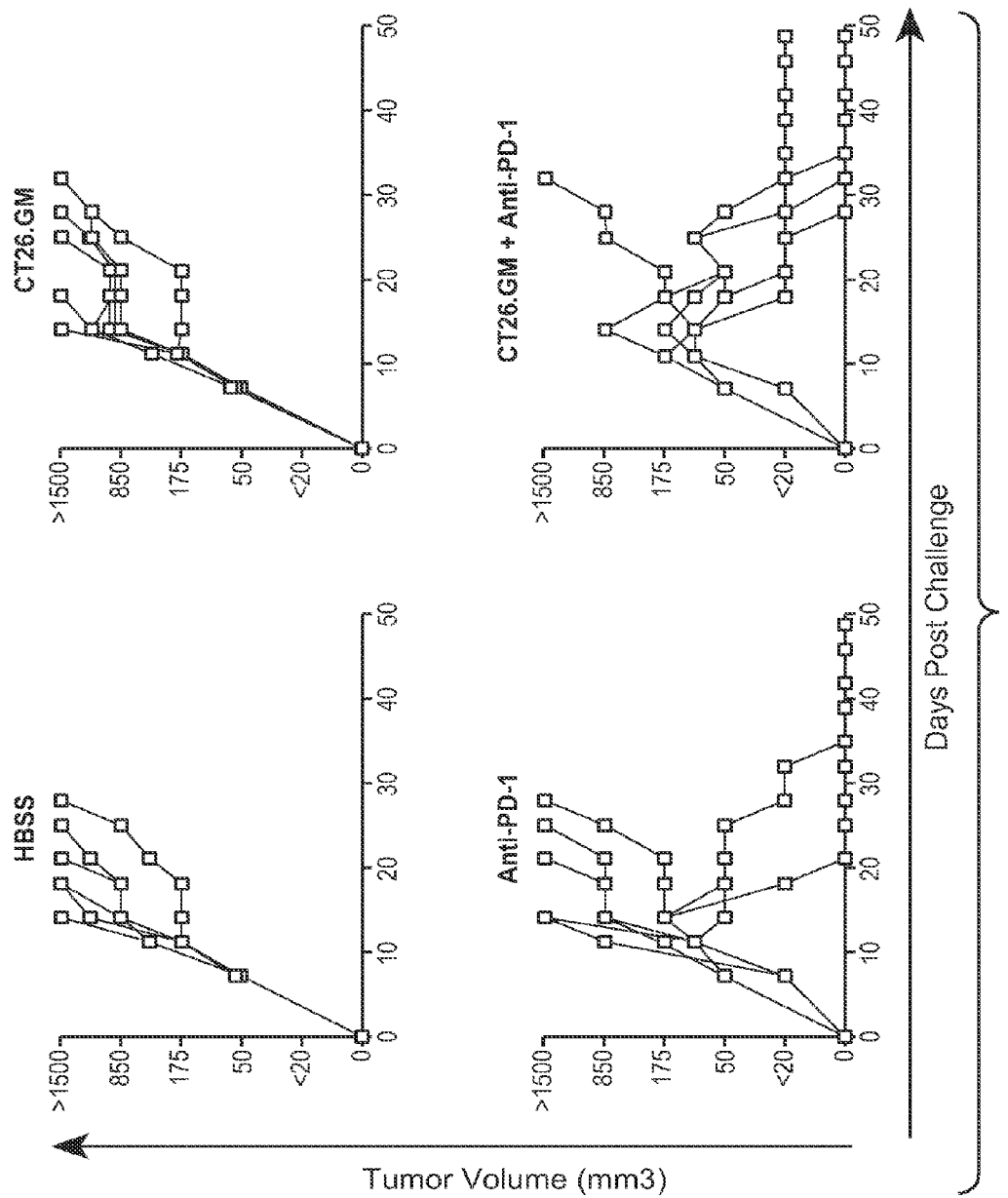
FIG. 5B illustrates the tumor burden of animals following administration of GM-CSF-secreting CT26 cells alone (CT26.GM), anti-PD-1 antibody alone (anti-PD-1) or CT26.GM in combination with an anti-PD-1 antibody when given on day 3 post tumor challenge.

As shown in FIGS. 5A and 5B, anti-PD-1 antibody and CT26.GM monotherapies both prolonged the survival of tumor bearing animals to 25 days compared to HBSS-injected control animals with a MST of 18 days. Consistent with the findings in the B16 model, CT26 tumor-bearing animals treated with the combination therapy showed a significant survival advantage over animals treated with either monotherapy, with 90% of animals surviving long-term (*p<0.01 compared to CT26.GM alone). Thus, anti-PD-1 antibody in combination with GM-CSF-secreting tumor cell immunotherapy significantly prolonged the survival of animals bearing either a non-immunogenic or an immunogenic tumor when compared to either monotherapy.

EXAMPLE 6

Enhancement of CD8+ T-cells in the Spleen Induced by GVAX/anti-PD-1 Combination Immunotherapy FIG. 6 illustrates the enhancement of the percentage of CD8+ T-cells in spleen from mice treated with GM-CSF-secreting B16F10 cells alone or in combination with an anti-PD-1 antibody. On day 0, mice were inoculated subcutaneously with live B16F10 cells. On day 3, $1 \times 10^6$ irradiated GM-CSF-secreting B16F10 cells (B16.Kd.GM) were injected as immunotherapy alone, or with 200 μg and 100 μg of anti-PD-1 antibody on days 3 and 4, respectively, as combination therapy. On day 10 following inoculation, spleens from mice were excised, digested and stained, and splenocytes were evaluated by flow cytometry. Shown are the percentage of T-cells positive for (A) CD4; (B) CD8; (C) CD11c; and (D) DX5. The percentage of CD8 positive T-cells are enhanced in B16.Kd.GM+anti-PD1 treated mice.

EXAMPLE 7

Enhancement of Memory T-cells in the Spleen Induced by GVAX/Anti-PD-1 Combination Immunotherapy FIG. 7 illustrates the percentage of memory T-cells in spleen from mice treated with GM-CSF-secreting B16F10 cells alone or in combination with an anti-PD-1 antibody. On day 0, mice were inoculated subcutaneously with live B16F10 cells. On day 3, $1 \times 10^6$ irradiated GM-CSF-secreting B16F10 cells (B16.Kd.GM) were injected as immunotherapy alone, or with 200 μg and 100 μg of anti-PD-1 antibody on days 3 and 4, respectively, as combination therapy. On day 10 following inoculation, spleens from mice were excised, digested and stained, and splenocytes were evaluated by flow cytometry. The percentage of memory T-cells was assessed by staining cells with for surface markers CD69 and Ly6C. Ly6C has been described as a marker for memory CD8+ T cells (Walumas et al., *J. Immunol.* 155:1973-1883 (1995) while CD69 is a marker for early T-cell activation. Memory T-cells were designated as the population of cells that were Ly6C+/CD69− within CD4 and CD8 positive cells. FIG. 7 shows the percentage of Ly6C+/CD69− cells within (A) the CD4 subpopulation; and (B) the CD8 subpopulation. The percentage of memory T-cells is significantly enhanced in spleens from mice treated with the B16.Kd.GM+anti-PD1 combination therapy compared to B16.Kd.GM immunotherapy alone.

EXAMPLE 8

Reversal of Anergy and Augmentation of Tumor-Specific T-cells Induced by GVAX/Anti-PD-1 Combination Immunotherapy On day 0, $1 \times 10^6$ OT-1 transgenic T-cells were adoptively transferred into C57BL/6 mice. The following day, mice were intravenously injected with 500 mg of SIINFEKL peptide to induce anergy in OT-1 cells. After establishing anergy, on day 11, mice were immunized with $1 \times 10^6$ irradiated GM-CSF-secreting B16 cells expressing ovalbumin as a surrogate antigen (GM.ova) as immunotherapy alone or immunotherapy was followed by 200 mg and 100 mg of anti-PD-1 antibody on days 11 and 12, respectively, as combination therapy. At indicated timepoints, peripheral blood leukocyte (PBL) from mice were drawn and evaluated for the percentage of antigen-specific T-cells by tetramer staining.

FIG. 8 illustrates an increase in the percentage of antigen-specific T-cells was induced by immunotherapy with both GM.ova and GM.ova plus anti-PD-1 antibody (16 days following adoptive transfer) following the establishment of anergy with SIINFEKL peptide. However, the percentage of antigen-specific T-cells was nearly 2-fold higher at day 16 in GM.ova plus anti-PD-1 antibody treated mice compared to mice treated with GM.ova alone. These data demonstrate that anti-PD-1 reverses anergy and augments tumor-specific T-cell response induced by GM-CSF tumor cell immunotherapy.

EXAMPLE 9

Antigen-Specific T-Cell Expansion Requires the Combination Therapy in Each Immunotherapy Boost Cycle To determine the optimal schedule for administration of each component of the combination therapy to expand antigen-specific T-cells effectively in a bi-weekly multi-treatment setting, three different combination therapy treatment schedules were evaluated.

To first establish an antigen-specific T-cell response, all B16 tumor-bearing animals received GM.ova immunotherapy and anti-PD-1 antibody at the first therapy cycle. On day 0, $1\times10^6$ ovalbumin-specific, transgenic T-cells (OT-1 cells) were adoptively transferred into tumor-bearing C57BL/6 mice that had been inoculated on day −1 with live $2\times10^5$ F10.ova cells. On day 3, mice were immunized with $1\times10^6$ irradiated GM-CSF-secreting B16 cells expressing ovalbumin (GM.ova) as immunotherapy alone or GM.ova immunotherapy was followed by 200 µg and 100 µg of anti-PD-1 antibody on days 3 and 4, respectively (the first therapy cycle). For subsequent therapy cycles, one group of animals received bi-weekly GM-ova and anti-PD-1 antibody, and another group received bi-weekly anti-PD-1 antibody with GM-ova administered with every other anti-PD-1 treatment (monthly).

Figure 9A:
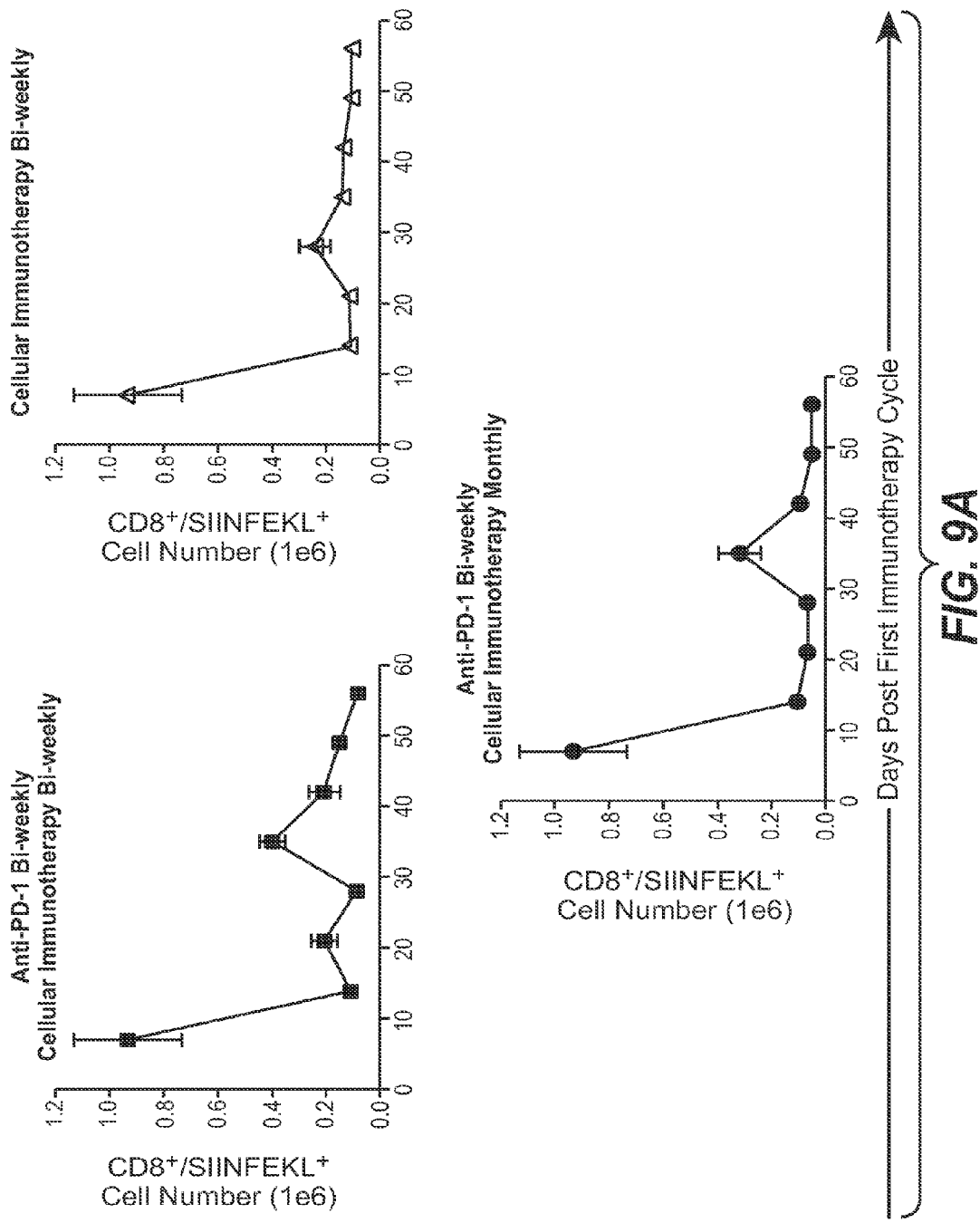
FIG. 9 illustrates the expansion and contraction of the population of ovalbumin-specific CD8 T-cells in spleens of mice treated with an initial therapy cycle of GM.ova immunotherapy, followed by either (i) anti-PD-1 and immunotherapy administered biweekly; (ii) GM.ova immunotherapy only administered biweekly; or (iii) anti-PD-1 administered biweekly and GM.ova immunotherapy administered monthly. Shown are the absolute numbers of ovalbumin-specific CD8 T-cells in the spleen by tetramer staining (A) and ovalbumin-specific CD8 T-cells co-stained with the activation marker CD107a (B) and IFN-γ (C).

At indicated time points, splenocytes from selected animals were isolated and evaluated for the presence of ovalbumin-specific CD8+ T-cells by co-staining the cells with anti-CD8 antibody and the SIINFEKL tetramer. The study showed the expansion and contraction of the population of ovalbumin-specific CD8 T-cells in the spleen after each treatment cycle (FIG. 9A) and that ovalbumin-specific CD8 T-cells expanded and peaked 7 days after each therapy cycle in animals that received the cellular immunotherapy and the PD-1 blockade concurrently. In animals that received bi-weekly cellular immunotherapy alone, the peak of ovalbumin-specific CD8 T-cell expansion from the second immunotherapy cycle was observed 2 weeks later (day 28). In contrast, in animals that received bi-weekly anti-PD-1 antibody and monthly GM.ova immunotherapy, the expansion of the ovalbumin-specific CD8 T-cells was only observed after the treatment cycle that consisted of the cellular immunotherapy and the PD-1 blockade and not when only the antibody was administered.

Figure 9B:
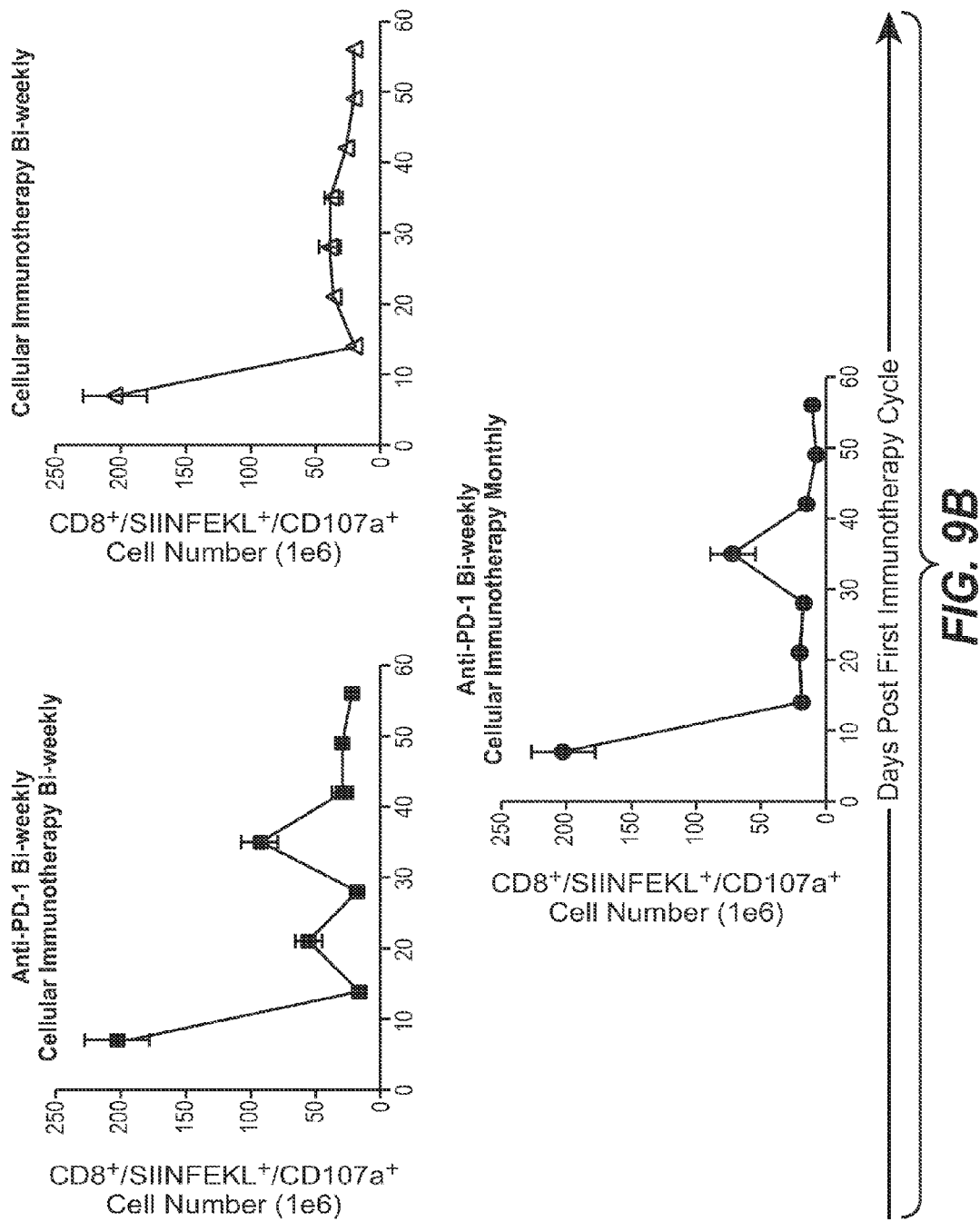
Figure 9C:
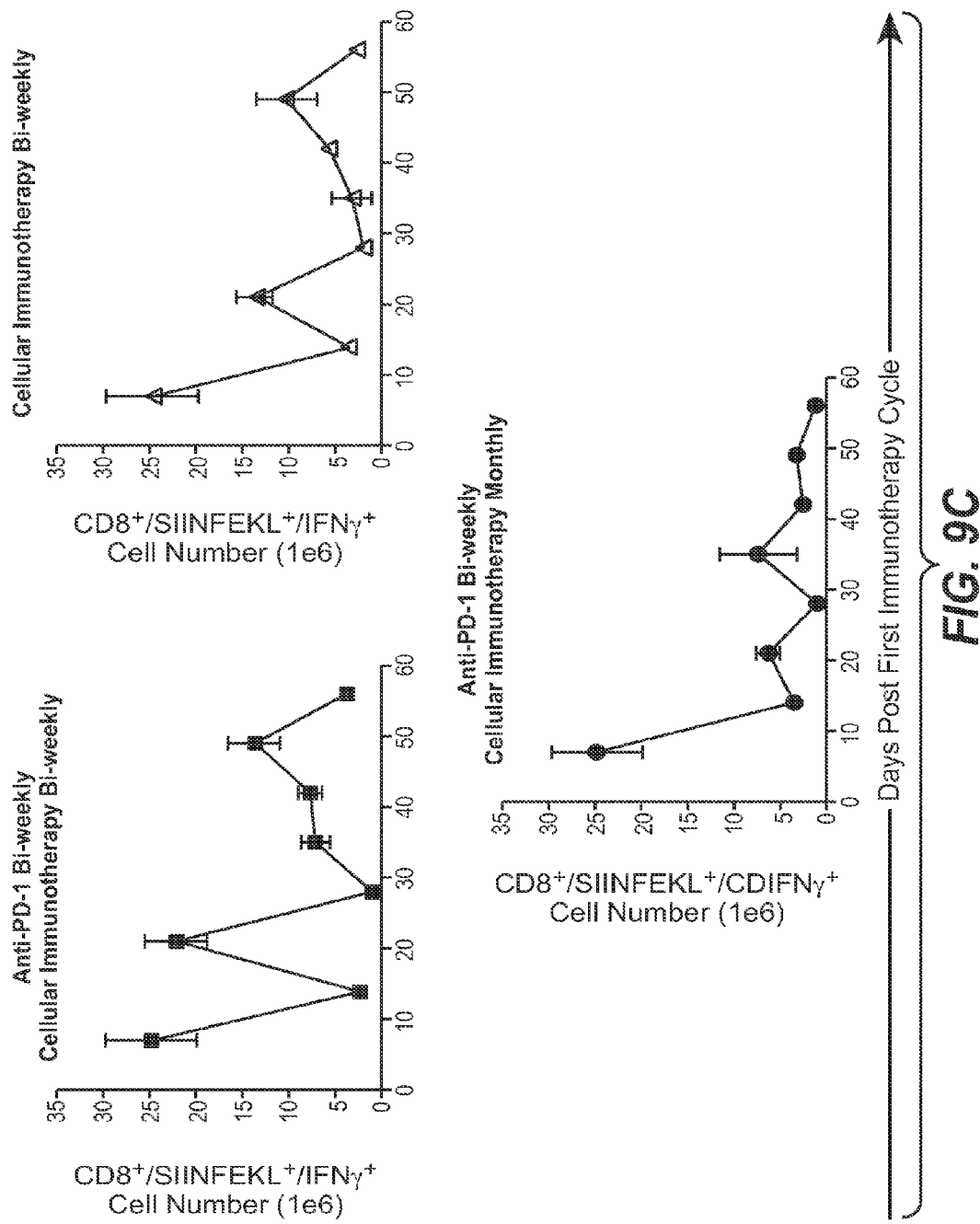

The effector phenotype of these ovalbumin-specific CD8 T-cells was confirmed by co-staining the cells with the activation markers, CD107a and IFNγ (FIGS. 9B and C). In animals that received the combination therapy at each therapy cycle, a similar trend in the number of tetramer-positive cells and the number of cells with an effector phenotype was observed. However, in animals that received bi-weekly cellular immunotherapy alone or bi-weekly anti-PD-1 antibody and monthly GM.ova immunotherapy, the peak of the IFNγ-secreting ovalbumin-specific CD8 T-cells did not always correlate with the peak of total ovalbumin-specific CD8 T-cells. After the second treatment cycle, in the bi-weekly cellular immunotherapy alone group, the number of IFNγ-secreting ovalbumin-specific CD8 T-cells peaked on day 21 while total ovalbumin-specific CD8 T-cells peaked on day 28. Similarly, in the bi-weekly anti-PD-1 antibody and monthly GM.ova immunotherapy group, the number of IFNγ-secreting ovalbumin-specific CD8 T-cells peaked on day 21 while total ovalbumin-specific CD8 T-cells did not change. After the second treatment cycle, the data showed that the combination therapy most efficiently expanded the number of IFNγ-secreting ovalbumin-specific CD8 T-cells ($21.92+/-3.31\times106$ cells) and that cellular immunotherapy alone ($13.57+/-1.95\times106$ cells) is more effective than anti-PD-1 antibody alone ($6.11+/-1.20\times106$ cells). In summary, these data suggested that readministration of the cellular immunotherapy with the anti-PD-1 antibody in subsequent immunotherapy cycles was required to reactivate these T-cell responses.

The present invention is not to be limited in scope by the exemplified embodiments, which are intended as illustrations of single aspects of the invention. Indeed, various modifications of the invention in addition to those described herein will become apparent to those having skill in the art from the foregoing description and accompanying drawings, Such modifications are intended to fall within the scope of the appended claims. All references cited herein are hereby incorporated by reference in their entireties.

What is claimed is:

1. A method of cancer immunotherapy comprising:
   administering a cytokine-expressing cellular immunotherapy comprising cells modified to express GM-CSF and a single chain antibody that specifically binds to human Programmed Death 1 (anti-PD-1) to a subject with cancer,
   wherein the modified cells are rendered proliferation-incompetent by irradiation, and
   wherein administration of the cells modified to express GM-CSF and the single chain antibody results in enhanced therapeutic efficacy relative to administration of an anti-PD-1 antibody alone or cells modified to express GM-CSF alone.

2. The method of claim 1, wherein the cytokine-expressing cellular immunotherapy comprises cells that are autologous to the subject.

3. The method of claim 1, wherein the cytokine-expressing cellular immunotherapy comprises cells that are allogeneic to the subject.

4. The method of claim 3, wherein the allogeneic cells are a tumor cell line selected from the group consisting of a prostate tumor line, a non-small cell lung carcinoma line and a pancreatic cancer line.

5. The method of claim 1, wherein the cytokine-expressing cellular immunotherapy comprises bystander cells.

6. The method of claim 1, wherein the subject is a human.

7. The method of claim 1, wherein the cancer is a prostate cancer.

8. The method of claim 1, wherein the cancer is a non-small cell lung carcinoma.

9. The method of claim 1, wherein the cancer is a melanoma.

10. The method of claim 1, wherein the cancer is a colorectal cancer.

11. The method of claim 1, wherein the cancer is a renal cell carcinoma.

12. The method of claim 1, wherein the cancer is an ovarian cancer.

13. The method of claim 1, wherein the cytokine-expressing cellular immunotherapy is administered subcutaneously.

14. The method of claim 1, wherein the cytokine-expressing cellular immunotherapy is administered intratumorally.

15. The method of claim 1, wherein the cytokine-expressing cellular immunotherapy is intradermally.

16. The method of claim 1, wherein the cytokine-expressing cellular immunotherapy is administered intravenously.

17. The method of claim 1, wherein enhanced therapeutic efficacy is measured by increased overall survival time.

18. The method of claim 1, wherein enhanced therapeutic efficacy is measured by increased progression-free survival.

19. The method of claim 1, wherein enhanced therapeutic efficacy is measured by decreased tumor size.

* * * * *